US011131627B2

(12) United States Patent
Bachalo

(10) Patent No.: US 11,131,627 B2
(45) Date of Patent: Sep. 28, 2021

(54) FUEL CONTAMINATION MONITOR

(71) Applicant: Artium Technologies, Inc., Sunnyvale, CA (US)

(72) Inventor: William D. Bachalo, Los Altos Hills, CA (US)

(73) Assignee: Artium Technologies, Inc., Sunnyvale, CA (US)

( * ) Notice: Subject to any disclaimer, the term of this patent is extended or adjusted under 35 U.S.C. 154(b) by 794 days.

(21) Appl. No.: 15/890,559

(22) Filed: Feb. 7, 2018

(65) Prior Publication Data
US 2019/0242814 A1 Aug. 8, 2019

(51) Int. Cl.
| | |
|---|---|
| *G01N 21/3577* | (2014.01) |
| *G01N 15/06* | (2006.01) |
| *F02D 41/22* | (2006.01) |
| *G01N 33/28* | (2006.01) |
| *G01N 21/85* | (2006.01) |
| *G01N 21/53* | (2006.01) |
| *G01N 15/02* | (2006.01) |
| G01N 21/47 | (2006.01) |
| G01N 15/00 | (2006.01) |

(52) U.S. Cl.
CPC ......... *G01N 21/3577* (2013.01); *F02D 41/22* (2013.01); *G01N 15/0227* (2013.01); *G01N 15/06* (2013.01); *G01N 21/53* (2013.01); *G01N 21/85* (2013.01); *G01N 33/2835* (2013.01); *F02D 2200/06* (2013.01); *G01N 2015/003* (2013.01); *G01N 2015/0053* (2013.01); *G01N 2015/0693* (2013.01); *G01N 2021/4711* (2013.01)

(58) Field of Classification Search
CPC ..................... G01N 21/3577; G01N 33/2835
See application file for complete search history.

(56) References Cited

U.S. PATENT DOCUMENTS

| | | | |
|---|---|---|---|
| 5,471,299 A | 11/1995 | Kaye et al. | |
| 6,532,067 B1 * | 3/2003 | Chang ................... | G01N 21/64 |
| | | | 250/461.1 |
| 7,162,057 B1 | 1/2007 | Roth et al. | |

(Continued)

OTHER PUBLICATIONS

Velcon Contaminant Analyzer VCA®, 1964-R8 Feb. 2011, 4 pages.

(Continued)

*Primary Examiner* — Eric S. McCall
*Assistant Examiner* — Timothy P Graves
(74) *Attorney, Agent, or Firm* — Womble Bond Dickinson (US) LLP

(57) ABSTRACT

An apparatus to detect contaminants in a fuel comprises an input to receive a fuel flow. A light scattering system is coupled to the input. An imaging system is coupled to the light scattering system. A memory is coupled to the imaging system. A processor is coupled to the memory. Output signals from the imaging and light scattering systems are transferred to the processor. The processor is configured to cause the light scattering system to monitor the light scattering intensity from the contaminants in the fuel flow. The processor is configured to cause the light scattering system to measure a light scattering intensity signal from the contaminants in the fuel flow. The processor is configured to generate a trigger signal to turn on the imaging system when the light scattering intensity is greater than a predetermined threshold.

24 Claims, 17 Drawing Sheets

(56) References Cited

U.S. PATENT DOCUMENTS

| | | | |
|---|---|---|---|
| 7,518,719 B2 | 4/2009 | Sprenger et al. | |
| 2007/0175269 A1* | 8/2007 | Sprenger | G01N 21/532 73/54.01 |
| 2008/0002200 A1 | 1/2008 | White et al. | |
| 2010/0315638 A1* | 12/2010 | Goohs | G01N 21/274 356/337 |
| 2017/0038288 A1 | 2/2017 | Ward et al. | |
| 2017/0370896 A1 | 12/2017 | Arifin et al. | |

OTHER PUBLICATIONS

Particle Sizing, Canty Process Technology, Document P/N: TA10629-1, Rev. 0, downloaded before Feb. 6, 2018.

PCT International Preliminary Report on Patentability for PCT/US2019/016911 dated Aug. 20, 2020, 12 pages.

PCT International Search Report for PCT/US2019/016911, dated Jul. 5, 2019, 5 pages.

PCT Written Opinion of the International Searching Authority for PCT/US2019/016911 dated Aug. 20, 2020, 10 pages.

\* cited by examiner

FUEL CONTAMINATION MONITOR

GOVERNMENT LICENSE RIGHTS

This invention was made with government support under Contract No. W56HZV-12-C-0269 awarded by U.S. ARMY Tank and Automotive Research, Development and Engineering Center (TARDEC). The government has certain rights in the invention.

FIELD

Embodiments of the invention relate to contamination monitoring. More particularly, embodiments of the invention relate to detection of contaminants in fuel.

BACKGROUND

Generally, fuel spends time in large storage tanks and is transferred frequently between various containers, pipe lines, and ships before it reaches a motor vehicle (a motorcycle, a car, a bus, a train, a ship, an aircraft or other motor vehicle). During storage and handling, fuel may be exposed to contamination sources of various types including water condensation and leakage, particulate contamination from various sources including sand, rust, paint chips, faulty handling, or other contamination sources. Typical contaminants are particulate matter and water. Free water (e.g., water which has not been dissolved or emulsified in the fuel) can freeze and plug the fuel screens, filters, and injectors leading to engine flameout and damage.

Typically, water contamination in fuels may come from a variety of sources—for example, a minor leakage during a refining process, from a cooling process before transportation, from free water deposits in low spots in a pipeline, from rainwater that leaks through seals in roof tanks, and from moist air that may condense in storage tanks that are vented. Water in the form of ice in the fuel system can result in the fuel flow blockage and cause significant engine failure and damage to the vehicle.

Particulate matter typically includes solid corrosion products such as scale and rust. Refinery processing, materials, and airborne particulate such as fine sand particulate may enter the tank vents or slip past the seals. Particulate from damage to fuel hoses and filters, and solids from microbial infestation are other sources of particulate contamination. These sediment particles can clog fuel filters, atomizer screens, and small passages in the fuel injector systems, which may cause fuel injection equipment to operate sluggishly or fail.

The other sources of contamination may include microbes. Particulate matter produced by microorganisms or microbes can block fuel systems. The solids formed by bio growth can plug fuel filters and other fuel system components.

Conventional filters and coalescer separators may fail to remove sufficient particulate matter and free water which can then reach the vehicle fuel tanks. Conventional tank sampling and other manual techniques for measuring fuel contamination are time-consuming—causing unacceptable delays—and are unreliable.

SUMMARY

Methods and apparatuses to detect contaminants in a fuel flow are described. For an embodiment, an apparatus to detect contaminants in a fuel comprises an input to receive a fuel flow. Light scattering and light extinction measurement systems are coupled to the input. An imaging system is coupled to the light scattering system. A memory is coupled to the imaging system. A processor is coupled to the memory. A fuel contamination recording and indicator means are coupled to the processor. A fuel flow shut-off signal may be provided to enable fuel flow termination. A fuel flow output is coupled to the apparatus. The processor is configured to cause the light scattering system to monitor the light scattering intensity from and light absorption and extinction by the contaminants in the fuel flow. The processor is configured to cause the light scattering system to measure a light scattering intensity from the contaminants in the fuel flow. The processor measures the light extinction and absorption by particulate in the fuel. A light scattering intensity ratio measurement at two selected angles is used to determine if only harmless bubbles are producing the scattered light and light extinction. The processor is configured to generate a trigger signal to turn on the imaging system when the light scattering intensity is greater than a predetermined threshold.

For one embodiment, a method to detect contaminants in a fuel comprises receiving a fuel flow, monitoring a light scattering intensity from the contaminants in the fuel flow using light scattering systems, measuring the light scattering intensity using the light scattering systems, and generating a trigger signal to turn on an imaging system when the light scattering intensity is greater than a predetermined threshold. The intensity of the light scattering signal is used to measure the concentration of contaminants by using a calibration means.

For one embodiment, a non-transitory machine-readable medium comprises data that when accessed by a data processing system, causes the data processing system to perform a method to detect contaminants in a fuel that comprises receiving a fuel flow, monitoring a light scattering intensity from the contaminants in the fuel flow using a light scattering system, measuring the light scattering intensity using the light scattering system, and generating a trigger signal to turn on an imaging system when the light scattering intensity is greater than a predetermined threshold. In another embodiment, a line-of-sight extinction using a long wavelength light source (1.5 to 3 µm) is used to detect large globules of water and as second means for detecting contaminants in the flow. In another embodiment, light scattering detectors are placed at selected angles to determine the type of particulate material, whether solid particulate, free water droplets or harmless bubbles. Line-of-sight extinction is required because large globules of water may be invisible to imaging and light scattering modules because of low interface-to-volume ratio and lack of local index of refraction gradients.

Other features and advantages of embodiments of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements, in which.

DETAILED DESCRIPTION

Figure 1:
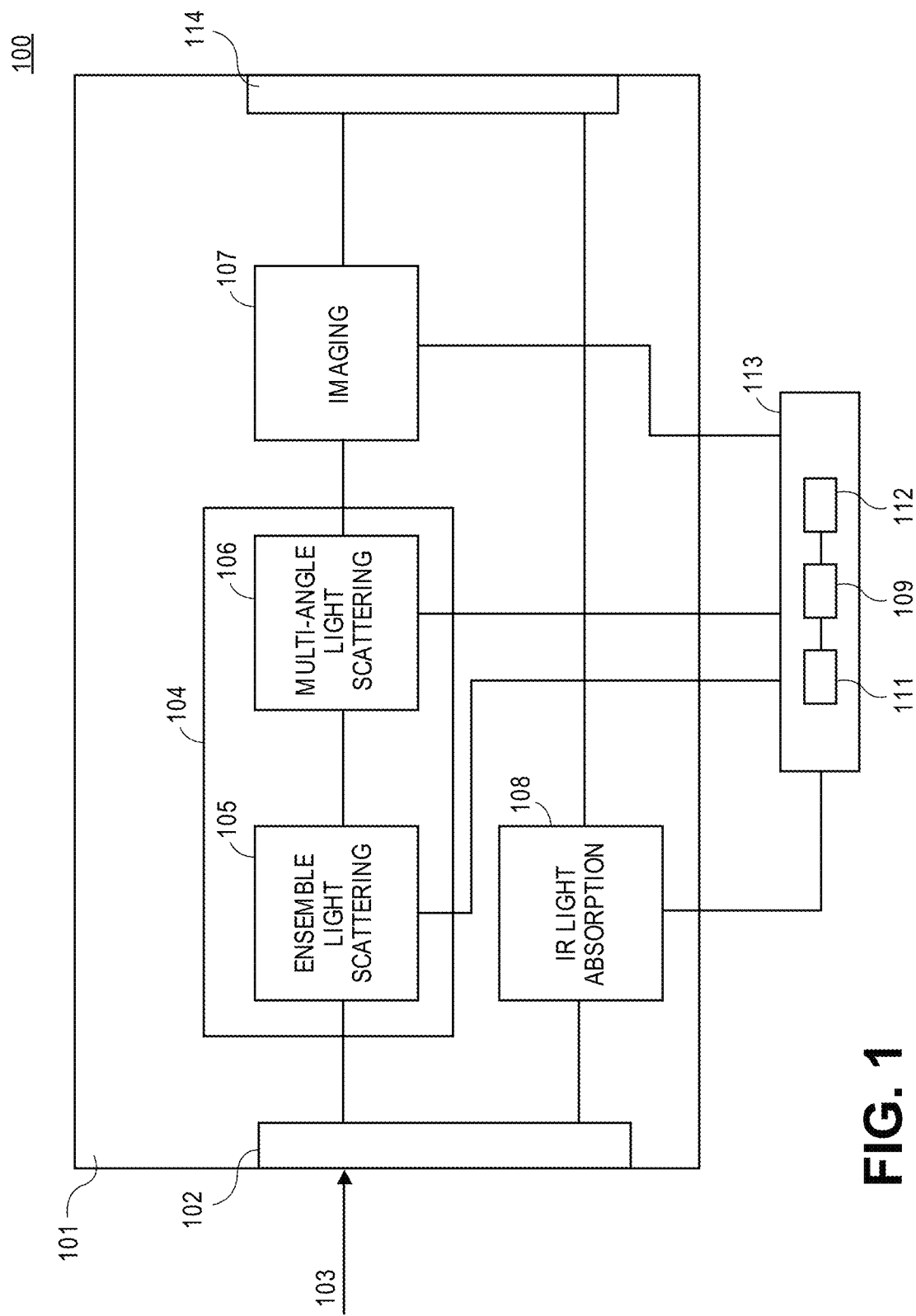
FIG. 1 shows a block diagram of one embodiment of an apparatus to detect contaminants in a fuel.

Methods and apparatuses to detect contaminants and measure their concentrations in a fuel are described. Contaminants can include free water droplets, solid particles, large volume water slugs (e.g., a water globe), or any other objects. Contaminants can have a spherical shape, a deformed spherical shape, an irregular shape, or any other shape. The contaminants can comprise a liquid (e.g., water or other liquid), solid material (e.g. fine sand, paint chips, rust, or other solid materials), microorganisms or any combination thereof. The fuel may also contain harmless air bubbles due to agitation and these bubbles will also produce a scattered light signal and a shadow image for the imaging system. These false detections need to be separated from the detection of contaminants.

Embodiments of an in-line monitoring system to test the fuel for particulate matter, condensed water, and gas bubbles are described. In-line monitoring during the fueling process is beneficial as fueling can be terminated immediately upon detection of contaminants, including particulate matter and water. An in-line monitoring system that tests the fuel for a particulate matter, condensed water, and gas bubbles and measures their concentration is a great benefit both to military and commercial aviation. An in-line monitoring system to detect and measure contaminants in a fuel flow is beneficial as in-line monitoring does not require filters that need to be changed periodically, or subjective judgements by manual inspection, that slow down the performance. An in-line system can also provide discrimination between the types of contaminants, a quantitative measure of their concentrations, and a size distribution for each particulate type.

For one embodiment, different types of contaminants—e.g., rust, paint, material from pipes and hoses, dust, sand, microbes, water, and gas bubbles—are monitored using light scatter detection methods. For some embodiments, the sizes of the contaminants that are detected by the system are in an approximate range from about 1 μm to about 500 μm. These methods provide very high sensitivity to particulate matter down to a few microns or smaller. The in-line monitoring system to test the fuel for particulate matter and condensed water uses modern solid-state light sources (diode lasers, light emitting diodes (LEDs), Vertical-Cavity Surface-Emitting Diode Lasers (VCSELs)) and detectors and is relatively inexpensive. For one embodiment, light scattering systems are built into a spool piece (e.g., a pipe) that is installed in-line with a fuel flow to detect the fuel contaminants in real-time.

For one embodiment, water droplets in the fuel are detected using light scattering systems. In addition to particulate matter and water droplets, bubbles can exist in the fuel. Typically, bubbles in fuel are acceptable. The light scattering systems are used to separate the light scattering signatures from particles, water droplets, and bubbles in the fuel. For one embodiment, free water in globules or slugs of liquid in the fuel are detected using an infrared light extinction/absorption technique, as described in further detail below.

For one embodiment, an in-line monitor is used to reliably detect particulate matter and water in suspension (free water droplets) without false detections produced by small bubbles in the fuel flow. The in-line monitoring system can be operated from a rechargeable battery source. Recharging may be accomplished by connecting to the refueling vehicle's electrical system. Optical sensors located in the fuel line or in a smaller sample line that is parallel to the fuel line are used to detect particulates and water in suspension (e.g., fuel) in real time. For one embodiment, the in-line monitoring system is connected to an alarm and a rapid shutoff valve to stop the fuel flow if the particulate matter and/or water content exceeds a prescribed threshold value, as described in further detail below.

FIG. 1 shows a block diagram of one embodiment of an apparatus 100 to detect contaminants in a fuel. Apparatus 100 comprises an enclosure 101. Enclosure 101 includes an input 102 to receive a fuel flow 103 and an output 114 to output the fuel flow. A light scattering system 104 is coupled to the input 102. Light scattering system 104 includes an ensemble laser light scattering system 105 and a multi-angle light scattering detection system 106.

For one embodiment, the light scattering system 104 includes at least one light source. The ensemble laser light scattering system 105 includes at least one laser source to provide an incident light to monitor contaminants in the flow and at least one receiver to receive a light scattered from contaminants in the flow. For one embodiment, the laser source of the ensemble laser light scattering system 105 operates at 660 nm wavelength, or other wavelength determined by design. The output power of this laser is about 120 mW. For one embodiment, the laser source of the ensemble laser light scattering system 105 includes one or more vertical cavity surface emitting diode lasers (VCSELs), edge emitting semiconductor lasers, or other laser sources. For one embodiment, the receiver of the ensemble laser light scattering system 105 includes a photodetector, e.g., a PIN photodiode with varying neutral density filters and an optical assembly to determine the probed volume of about few millimeters. For one embodiment, the photodetector is coupled to an amplifier to optimize the dynamic range of the receiver.

The ensemble light scattering system 105 is used to assess the concentration of contaminants once the contaminants size distribution is known. The ensemble scattering signal intensity provides the basis for concentration calculations by weighing the signal with the size distribution detected by the imaging system and using calibration information. At this stage, the concentration of individual contaminants is obtained based on the statistics gathered by the imaging system. In addition, the imaging system can provide comparative contaminants concentrations by taking into account the volume probed by the optics.

For one embodiment, multi-angle light scattering system 106 includes a light source to illuminate the probe volume. Two photodetectors are used to monitor the light scattered from the contaminants passing within the probe volume at two different angles. The signal intensities from these two detectors are then compared to separate bubbles from water or solid particles and to separate water droplets from solid particles.

For one embodiment, the multi-angle light scattering system 106 includes a laser source to provide an incident light to monitor contaminants in the flow and two receivers to receive a light scattered from the contaminants in the flow at two different angles, as described in further detail below. For one embodiment, the laser source of the multi-angle light scattering system 106 operates at 450 nanometers (nm), 532 nm, 630 nm, or at other wavelengths determined by design. For one embodiment, the output of the laser source of the light scattering intensity ratio system 106 is collimated into a narrow light beam having a diameter of about 100 μm, or other diameters determined by design. The laser source of the light scattering intensity ratio system 106 produces a light beam intensity of about 50 mW, or other light beam intensities determined by design. For one embodiment, the laser source of the light scattering intensity ratio system 106 includes one or more vertical cavity surface emitting diode lasers (VCSELs), edge emitting semiconductor lasers, or other laser sources.

As the light scattering intensity ratioing techniques involve comparing the relative amplitudes of two light signals at two angles, the laser output power can vary within 10% or more without affecting the results. Light scattered from the probe volume at each of the two scattering angles is then directed into a receiver (photodetector) device. For one embodiment, the receivers of the light scattering intensity ratio system 106 include photomuliplier tubes, arrays of avalanche photodiodes (APDs), PIN diodes, or any combination thereof.

An imaging system 107 is coupled to the light scattering system 104. For one embodiment, imaging system 107 includes a light source, a lens assembly, and an image sensor. For one embodiment, imaging system 107 includes at least one of a pulsed laser source, a pulsed light emitting diode (LED) source, or any combination thereof of sources to provide an incident light to contaminants in the fuel flow and a receiver to receive the light scattered from contaminants in the fuel flow. For one embodiment, the pulsed laser source of the imaging system 107 includes one or more vertical cavity surface emitting diode lasers (VCSELs), edge emitting semiconductor lasers, or other laser sources. For one embodiment, the receiver of the imaging system 107 includes one or more complementary metal oxide semiconductor (CMOS) or CCD cameras. The imaging system 107 provides reliable size information of the free water droplets, solid particles, and gas/air bubbles. This size information is needed in conjunction with the ensemble light scattering system data to enable an accurate measurement of the concentrations of each of the types of contaminants, e.g., free water droplets, solid particles, and gas/air bubbles. The imaging system 107 is configured to determine if the contaminant is a solid particle, water droplet or a gas bubble. For one embodiment, the imaging system 107 is used to separate water droplets that have substantially a spherical shape from solid particles that have a shape that is different from the spherical shape. Typically, different contaminants have different size distributions and morphology (e.g., spherical or irregular shape) in the fuel. The different contaminants have different scattering characteristics to produce different shadow images. For one embodiment, the imaging system 107 is configured to determine if the contaminant is a solid particle, a bubble, or a water droplet based on the shadow images.

For one embodiment, the light source of the imaging system 107 is sufficiently intense and is pulsed in very short durations to "freeze" the particle motion, and provide sharp images. For one embodiment, the light source of the imaging system 107 is a single 50 lumen (or 1 W) LED to provide a bright and homogenous image background. For one embodiment, the control signal for the LED has a fixed pulse duration and rate.

An infrared (IR) light absorption system 108 is coupled to the input 102. For one embodiment, infrared (IR) light extinction/absorption system 108 includes at least one IR laser source to provide an incident light to monitor the flow for a large volume of water and a receiver to measure the light intensity of the light beam after it is transmitted through or reflected by the large volume of water in the flow. For one embodiment, infrared (IR) light extinction/absorption system 108 is configured to detect discrete globules of water with the size of water globules that are greater than 100 μm to 1000 μm.

Typically, large slugs of water may be present in the fuel, especially when fueling from facilities located near frontline operations. IR light absorption system 108 is needed to identify large slugs of water due to coalescer breakdown and to provide additional information on the free water concentration in the fuel. IR light absorption system 108 uses a highly sensitive technique that provides a real-time response to changes in the free water concentration over a relatively large portion of the fuel. IR light absorption system 108 provides a measurement over a fairly large path length in the fuel. Thus, with a relatively large laser beam diameter, IR light absorption system 108 samples a much larger volume of fuel than the light scattering system or imaging system per unit time. The light scattering system or imaging system samples free water concentration based on the number of droplets passing the entire exposed laser beam in the fuel. Globules of water that are larger than the sample volumes for the imaging, light scattering intensity ratio, and ensemble light scattering methods may not be detected by systems 104 and 107. The globules of water cause a very large amount of light extinction/absorption which is indicated as a strong transient drop in the signal voltage from the photodetector of the IR light absorption system 108. Generally, an amount of light extinction is substantially equal to a sum of light scattering amount and light absorption amount. IR light absorption system 108 provides a reliable detection of water globules and other large (e.g., as large as on the order of millimeters) contaminants in the fuel. For one embodiment, IR light absorption system 108 includes a laser source operating at an IR wavelength—e.g., in an approximate range from about 1 μm to about 3 μm—or other IR wavelength. IR light absorption system 108 includes an IR detector. For one embodiment, the laser output of the IR light absorption system 108 is a stable output at about 5 mW, or at other power based on design. That is, the IR absorption of water is used to identify large water content not appropriately distinguished by the scattering or imaging systems or in addition to these systems for redundant measurements. For one embodiment, the IR extinction/absorption signal is compared to a visible light extinction signal to identify large water content from other contaminants, such as solid particles, water droplets, or bubbles.

The apparatus 100 integrates information from each of the systems 105, 106, 107, and 108 to obtain particle size distributions for solid particles, free water, and bubbles, if they are present. The concentration of bubbles is measured to ensure that the bubbles are not producing a false shut off condition based on the measured ensemble light scattering concentration. For example, the ensemble scattering system 105 provides information about total concentrations of contaminants. The apparatus 100 uses at least one of light scattering intensity ratio system 107 and imaging system 107 to identify bubbles from other contaminants, determines a percentage of bubbles in the fuel flow, and provides a separation of counts and size of bubbles versus solid particles and free water. Apparatus 100 uses ensemble light scattering system 105, light scattering intensity ratio system 106, and imaging system 107 to measure sizes, concentrations, and other characteristics of the solid particles. For one embodiment, apparatus 100 is configured to measure the sizes of the measured particles in an approximate range from about 1 μm to about 150 μm, or in other ranges. For one embodiment, apparatus 100 is configured to measure particle densities in an approximate range from about 0.81 g/cm$^3$ to about 5.24 g/cm$^3$, or in other ranges.

As shown in FIG. 1, apparatus 100 comprises a processing system 113. For one embodiment, at least a portion of the processing system 113 is within enclosure 101. For another embodiment, at least a portion of the processing system 113 is outside enclosure 101. The processing system 113 includes a processor 109 coupled to a memory 111 and a display 112. Processing system 113 is coupled to the ensemble laser light scattering system 105, multi-angle light scattering system 106, imaging system 107, and IR light absorption system 108. The processor 109 is configured to cause the light scattering system 104 to monitor the light scattering intensity of the fuel flow 103. The processor 109 is configured to cause the light scattering system 104 to measure a light scattering intensity of the particulate in the fuel flow. The processor 109 is configured to generate a trigger signal to turn on the imaging system 107 when the intensity of the light scattered from the particulate in the fuel flow are greater than a predetermined threshold.

For one embodiment, the processor 109 is configured to cause the light scattering system 104 to continue to monitor the light scattering intensity of the fuel flow 103 and to cause the output 114 to output the fuel flow when the light scattering intensity is not greater than a predetermined threshold. For one embodiment, the processor 109 is configured to determine sizes of the contaminants, types of the contaminants, or both the sizes and the types of the contaminants in the fuel flow 103. For one embodiment, the processor 109 is configured to determine a concentration of the contaminants based on at least one of the sizes and the types of the contaminants in the fuel flow 103.

For one embodiment, the processor 109 is configured to measure an infrared absorption signal of the fuel flow 103 using the IR light extinction/absorption system 108. The processor 109 is configured to shut off the fuel flow if the infrared absorption signal is less than a predetermined infrared absorption signal, as described in further detail below.

The ensemble laser light scattering system 105, multi-angle light scattering system 106, imaging system 107, and IR light absorption system 108 work together using four different techniques. The ensemble laser light scattering system 105 is used to measure the intensity of light scattered by an ensemble of contaminants that include particles, bubbles, and droplets in the fuel flow 103. The multi-angle light scattering system 106 is used to measure the light intensity of the light scattered by the contaminants in the fuel flow 103 at a plurality (e.g., two, three, or more) different angles for a probe volume. The system 106 also measures the concentration and type of the contaminants with the assumption that there is a substantially high probability that only one particle passes the probe volume at a time. Another embodiment measures the ensemble light scattering intensity ratio at two angles to determine if the light is scattered by air bubbles or contaminants. The light absorption system 108 operates based on different absorbance of the IR light by different types of the contaminants. Typically, as light scattering system 105, multi-angle light scattering system 106, and imaging system 107 work based on interface detection, these systems may fail to detect a large volume of water or other liquid in the fuel flow 103. The light extinction/absorption system 108 is used to detect a large volume of water in the fuel flow 103.

The apparatus 100 to monitor contaminants in a fuel uses a plurality of optically-based techniques to comprehensively and reliably detect and quantify fuel contaminants. An ensemble light scattering system 105 is used to obtain reliable measurements of total particulate concentration including free water droplets, solid particulate, and gas bubbles. As gas bubbles scatter light but do not have negative affect in terms of fuel contamination, gas bubbles need to be separated from other light scatterers. Typically, air bubbles are not easily discriminated by conventional techniques as the air bubbles produce light scattering signals similar to that of the contaminants. The apparatus 100 uses a multi-angle light scattering technique of the multi-angle light scattering system 106 to separate gas bubbles from free water droplets or solid particles. The apparatus 100 uses a high-resolution imaging system 107 to determine the size and type of the contaminants. The size measurements provided by the imaging technique for all scatters are used in conjunction with the ensemble light scattering technique to produce a reliable particulate mass concentration in the fuel. An IR line-of-sight absorption module 108 complements the other diagnostics to detect large slugs of water which may be missed by the light scattering or imaging techniques.

For one embodiment, the apparatus 100 monitors the fuel passing through the system at all time to prevent the presence of contaminants which can be responsible for engine filter and fuel injector clogging or failure. Operating different techniques to identify and quantify the different contaminants at once may be too energetically demanding for 24 hour operation on batteries. For one embodiment, the system uses low consumption laser-based methods of the light scattering system 104 to monitor the fuel, while more power-hungry components such as cameras and associated processing components of the imaging system 107 are kept at idle while the fuel is clean.

Figure 2:
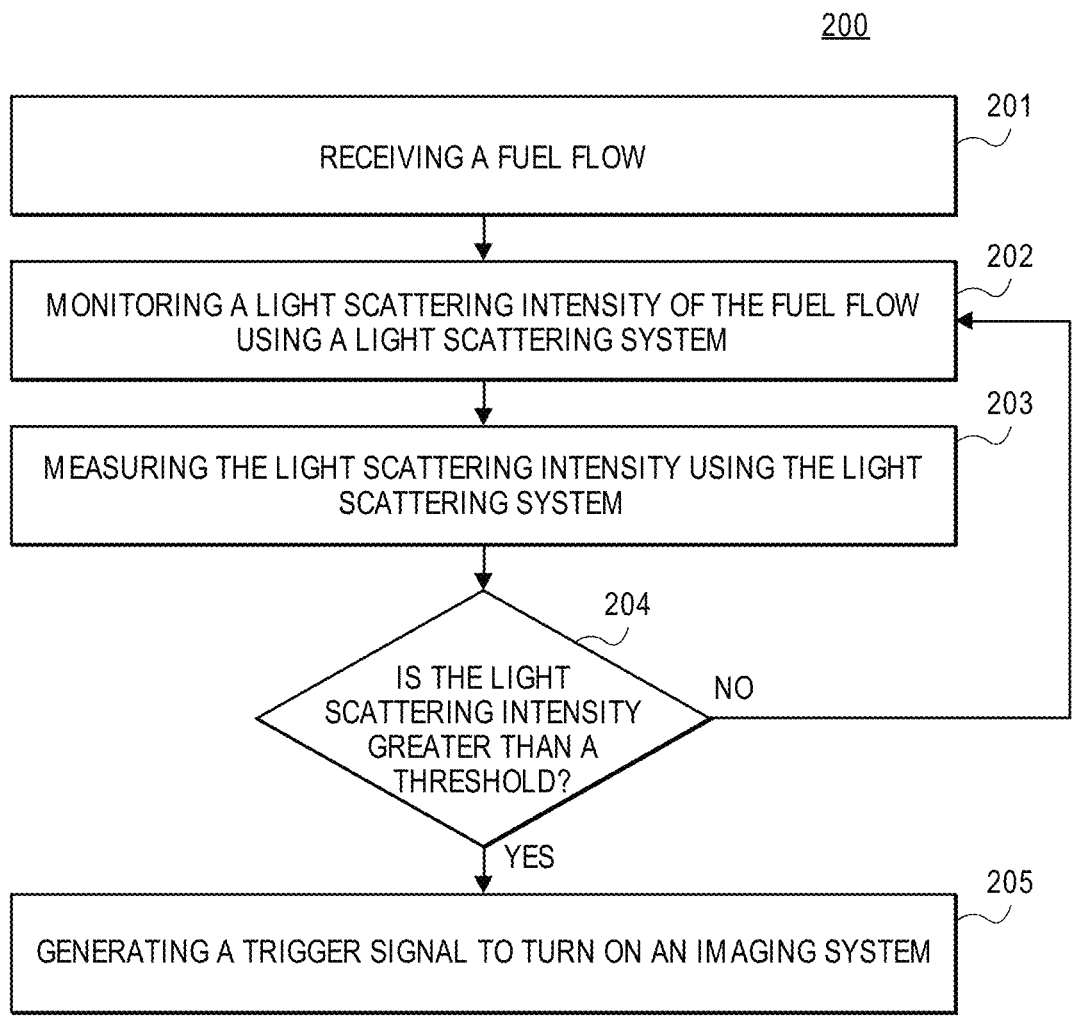
FIG. 2 shows a flow chart of one embodiment of a method to detect contaminants in a fuel.

FIG. 2 shows a flow chart of one embodiment of a method 200 to detect contaminants in a fuel. The method 200 begins with an operation 201 that involves receiving a fuel flow 103. At an operation 202 a light scattering intensity of the fuel flow is monitored using a light scattering system 104. At an operation 203 the light scattering intensity of the fuel flow is measured using the light scattering system 104. At operation 204 it is determined if the light scattering intensity of the fuel flow 103 is greater than a predetermined threshold. If the light scattering intensity is not greater than the predetermined threshold, method 200 returns to operation 202. If the light scattering intensity of the fuel flow 103 is greater than the predetermined threshold, a trigger signal is generated to turn ON imaging system 107.

A method to detect contaminants in the fuel starts with measuring the actual size distribution of the contaminants using imaging system 107 for a short period of time. At the same time the data from the ensemble laser light scattering system 105 and multi-angle light scattering system 106 are recorded. The multi-angle light scattering system 106 probes a single contaminant at a time, while the ensemble scattering system 105 quantifies scattering intensity of an ensemble of contaminants to obtain information on the contaminant concentration.

After the imaging system 107 is turned off, the imaging system data are used by the light scattering system 104 to monitor the consistency of the fuel condition. During this time, it is assumed that the normalized size distribution of the contaminants remains unchanged while ensemble laser light scattering system 105 is monitoring the concentration of the contaminants and multi-angle light scattering system 106 is monitoring the share of each contaminant type. As soon as the module 105, module 106, or both module 105 and module 106 sense that a deviation from the initial accepted condition is greater than a predetermined threshold, the imaging system 107 is turned on again to inspect the new condition. If the imaging system 107 senses a deviation from the initial accepted condition is greater than a predetermined threshold, a shut off command is issued to shut off fueling. For one embodiment, IR absorption system 108 works in parallel with and independent from light scattering system 104 and the imaging system 107.

Figure 3:
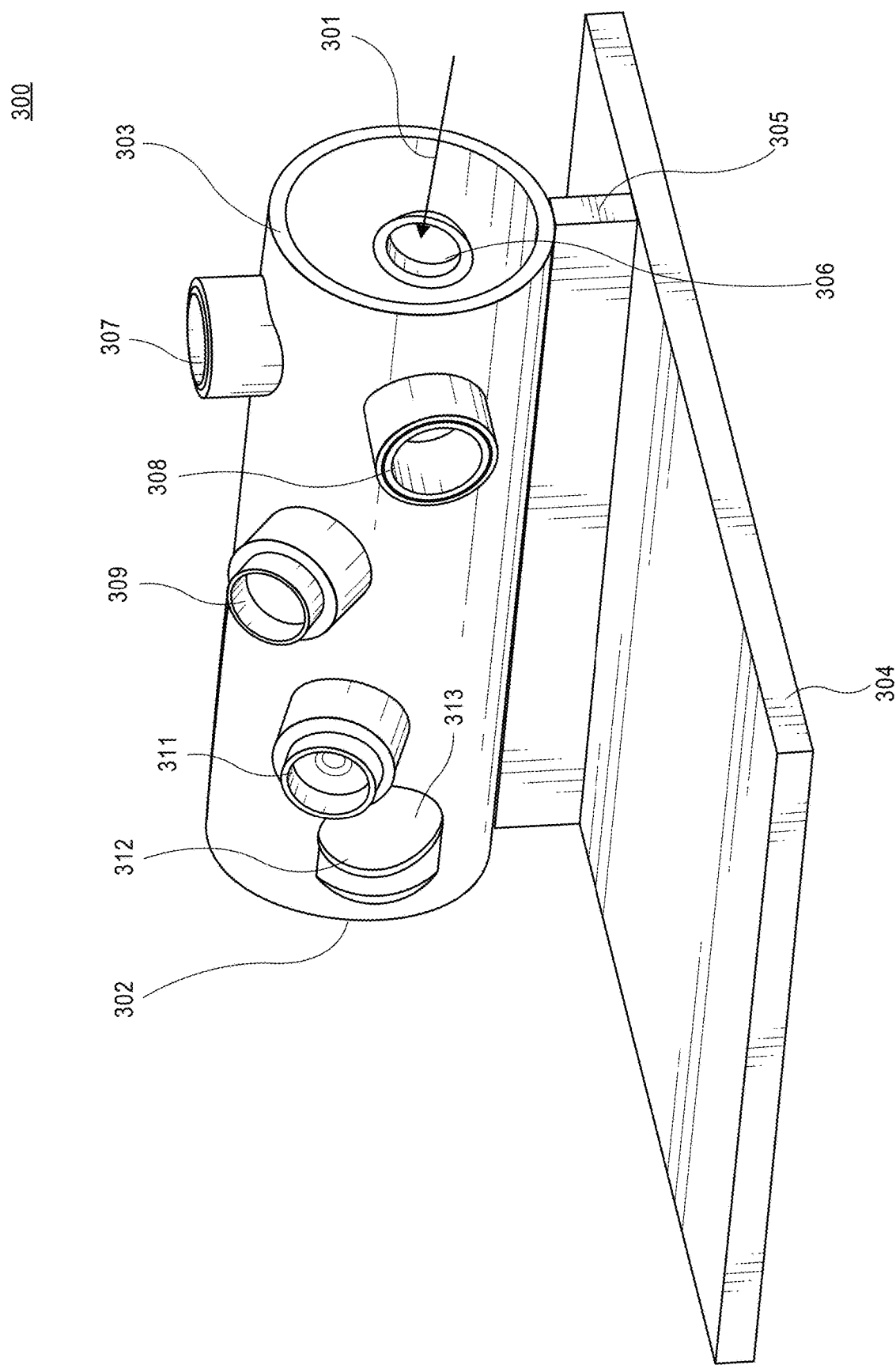
FIG. 3 is a view illustrating one embodiment of a portion of a system to detect contaminants in the fuel.

FIG. 3 is a view 300 illustrating one embodiment of a portion of a system to detect contaminants in the fuel. As shown in FIG. 3, a pipe 303 is attached to a top of a stand 305 that is attached to a base plate 304. The pipe 303 includes an input 301 to receive a fuel flow and an output 302 to output the fuel flow. Pipe 303 includes a plurality of windows such as a window 307, a window 308, a window 309, a window 311, a window 312 and a window 313.

For one embodiment, a fuel flow enters the system through a camlock fitting which leads to a metal pipe, such as pipe 303. For one embodiment, the pulses of light provided by one or more light sources of the system have a duration of about 0.05 microseconds (μsec), or other pulse durations. For one embodiment, the diameter of the pipe 303 is about 3 inches, or any other diameter determined by design.

For one embodiment, the base 304 is an aluminum plate that has the thickness of about ½ inch, or any other thickness determined by design that provides a strong foundation for the entire system to be built on. The stand 305 is fastened onto base 304 with screws. The main pipe 303 is dip-brazed on top of the stand 305. For one embodiment, the stand is an aluminum stand that has the thickness of about ½ inch, or any other thickness determined by design. The reason of choosing dip-brazing over other types of connection is to form a structure that can sustain all of the components in the system without concern for misalignment. For one embodiment, the length of the main pipe 303 is about 255 millimeters (mm).

The main pipe 303 has a plurality of windows, such as windows 307, 308, 309, 311, 312, and 313. Some of the windows are used to provide the incident light beams from light sources to contaminants in the fuel flow. Some of the windows are used to receive the light scattered, reflected, or scattered and reflected from the contaminants in the fuel flow.

Some of the light windows are used to provide the incident light beams from laser sources and at least one of the light windows is used to provide the incident light from a light emitting diode (LED) probe. For one embodiment, some of the windows of the pipe 303 are used for receivers of the multi-angle light scattering system 106 to sense the lights at least two different angles. For one embodiment, at least one of the windows of the pipe 303 is used for a receiver of the ensemble laser light scattering system 105 and at least one of the windows of the pipe 303 is used for a receiver of the IR light absorption system 108.

Figure 4:
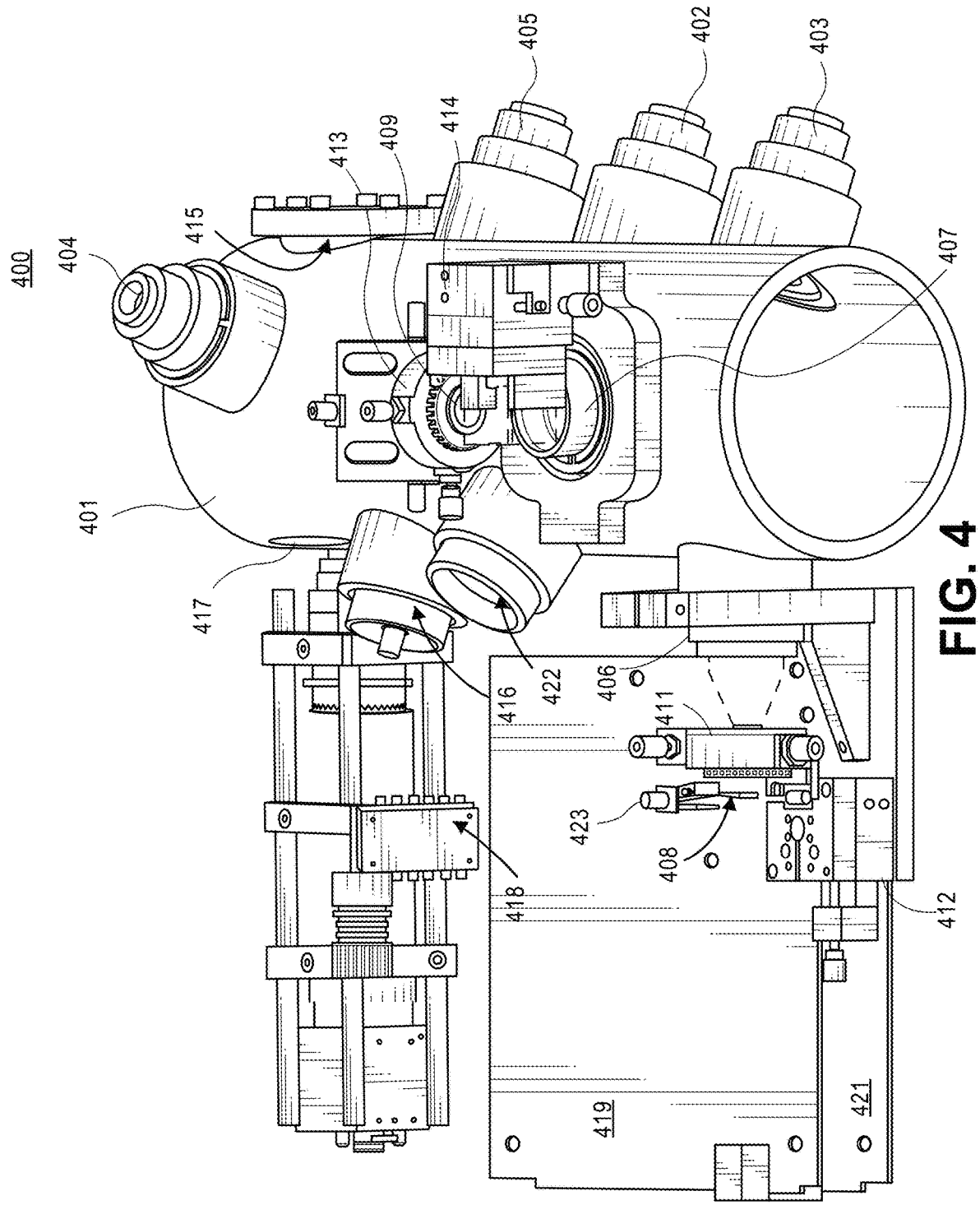
FIG. 4 is a view illustrating one embodiment of a system to detect contaminants in the fuel flow.

FIG. 4 is a view 400 illustrating one embodiment of a system to detect contaminants in the fuel flow. As shown in FIG. 4, a pipe 401 includes a window 405 to provide an incident light from a laser source of the ensemble light scattering ensemble laser light scattering system to detect contaminants in the fuel flow. Pipe 401 includes a window 403 to provide an incident light from a laser source of the light scattering intensity ratio system to detect contaminants in the fuel flow. Pipe 401 includes a window 404 to provide an incident light from a laser source of the imaging system to detect contaminants in the fuel flow. Pipe 401 includes a light probe window 415 to provide an incident light from a light source (e.g., an LED, a laser diode, a VCSEL laser, or other light source of the imaging system to detect contaminants in the fuel flow.

For one embodiment, one or more VCSELs are used as a light source for the multi-beam imaging system to achieve high quality illumination that is uniform and free of laser speckle. Generally, VCSELs have lower manufacturing costs and are highly reliable as compared to edge emitter diode lasers. Generally, a semiconductor laser includes layers of semiconductor material grown on top of each other on a substrate. For edge emitter laser diodes, light oscillates parallel to the layers of semiconductor material and escapes sideways resulting in an elliptical laser beam profile. VCSELs have a number of advantages over edge emitting laser diodes including their ability to operate at relatively high temperatures so cooling systems are not required.

Pipe 401 includes a window 405 to provide an incident light from a laser source of the IR light absorption system to detect contaminants in the fuel flow. Pipe 303 represents a portion of the pipe 401. As shown in FIG. 4, pipe 401 includes a window 422 for a receiver of the ensemble laser light scattering system to sense the light scattered from contaminants in the fuel flow. As shown in FIG. 4, window 422 is at the opposite side of the pipe 401 relative to the window 402.

As shown in FIG. 4, pipe 401 includes a window 407 for a receiver 409 of the light scattering intensity ratio system and a window 406 for a receiver 408 of the light scattering intensity ratio system. As shown in FIG. 4, receiver 409 and receiver 408 are positioned at different angles relative to a central axis of the pipe 303 to receive the light scattered from the contaminants in the fuel flow at different angles. As shown in FIG. 4, window 406 is at the opposite side of the pipe 401 relative to the window 403 and at an angle relative to window 403 and window 407 is positioned at a different angle relative to window 403. As shown in FIG. 4, receiver 408 is coupled to a movable stage 412 and receiver 409 is coupled to a movable stage 414. For one embodiment, each of the movable stages 412 and 413 is configured to move along at least two axes—e.g., a horizontal axis and a vertical axis—to adjust a position of the receiver relative to the window of the pipe 401. For one embodiment, each of the movable stages 412 and 413 is configured to rotate around at least one axes to adjust a position of the receiver relative to the window of the pipe 401. Movable stage 412 is coupled to a lens holder 411 and movable stage 414 is coupled to a lens holder 413. As shown in FIG. 4, receiver 408 receives the light that passes through one or more lenses on lens holder 411 and receiver 409 receives the light that passes from one or more lenses on lens holder 413.

As shown in FIG. 4, the pipe 401 includes a window 417 for an imaging probe receiver of the imaging system to sense the light scattered, reflected, or scattered and reflected from contaminants in the fuel flow. As shown in FIG. 4, the imaging probe window 417 is on the opposite side of the light probe window 415 for a microscope objective to be inserted into the flow. As shown in FIG. 4, the microscope objective of the image probe receiver inserted through window 417 is coupled to a holder 418. As shown in FIG. 4, the imaging probe is integrated into the main flow that enters the pipe 303 to ensure real time measurements. For another embodiment, the imaging probe system acquires photographs of a side stream sampled from the main flow. The side stream flows through a narrow tube coupled to the pipe 301 and then between two closely placed glass slides.

Figure 5:
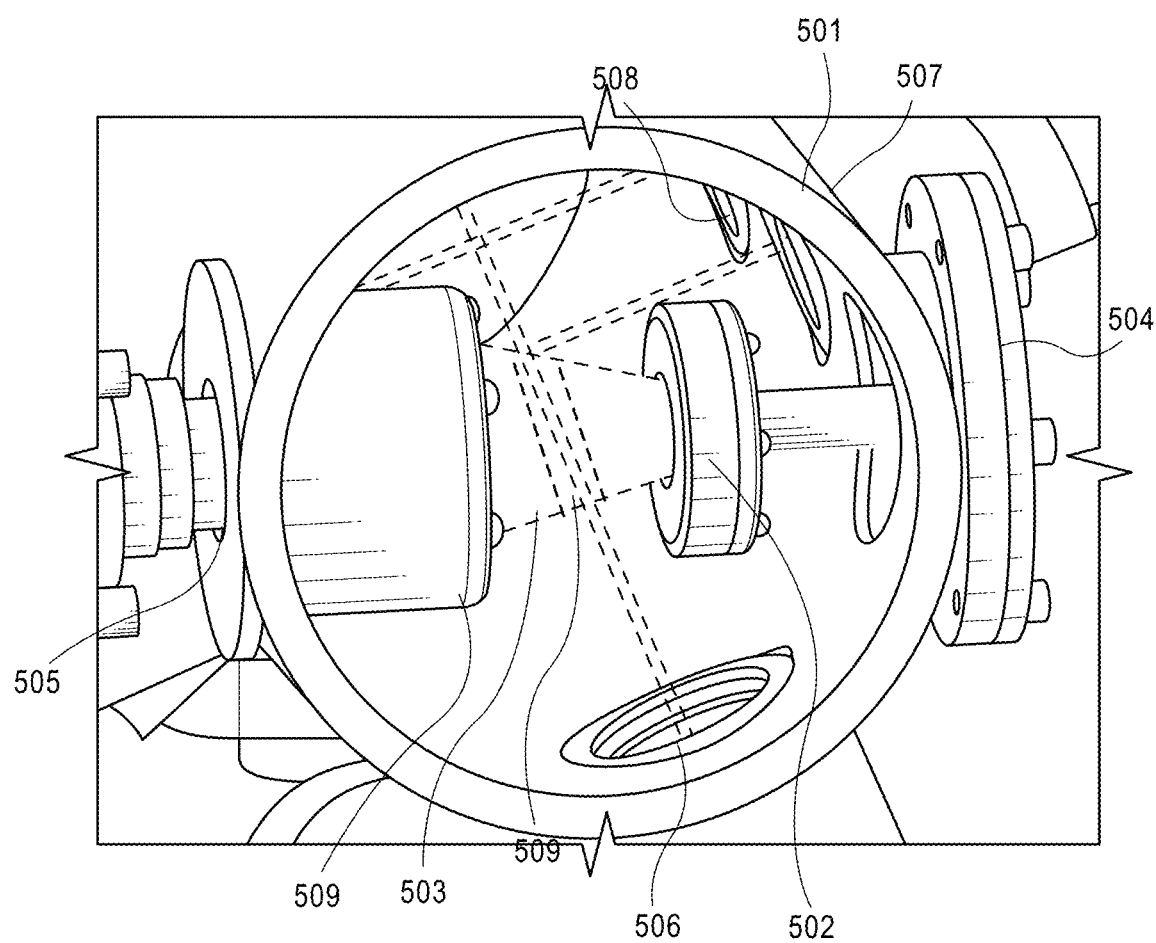
FIG. 5 is a view illustrating one embodiment of a portion of an imaging probe.

For one embodiment, the illumination light source of the imaging system includes one or more LEDs. For one embodiment, the illumination light source of the imaging system is a pulsed light source. For one embodiment, the power of the pulsed LED of the imaging system is about 50 lumen (or about 1 Watt (W)). For one embodiment, the pulsed LED of the imaging system provides pulses of light with duration of about 0.05 microseconds (µsec), or other pulse duration. The pulsed LED probe is installed substantially close to the microscope objective, as shown in FIG. 5. For one embodiment, the illumination light source of the imaging system includes one or more laser diodes, vertical-cavity surface-emitting (VCSEL) lasers, or other illumination sources.

FIG. 5 is a view illustrating one embodiment of a portion of an imaging probe. As shown in FIG. 5, a pipe 505 a plurality of windows, e.g., windows 504, 505, 506, 507, and 508. For one embodiment, the windows 506, 507, and 508 are light source windows to provide incident light beams, as described above. As shown in FIG. 5, window 504 is a light probe (e.g., LED, diode laser, VCSEL laser, or other light probe) window and window 505 is an imaging probe window. For one embodiment, pipe 501 represents a portion of pipe 401, imaging probe window 505 represents imaging probe window 417 and light probe window 504 represents light probe window 415. As shown in FIG. 5, imaging probe window 505 is opposite to the light probe window 504. A pulsed LED source on a holder 502 is inserted through opening (window) 504 deep into the flow close to the centerline of the pipe 501 to provide an incident light 503 to create a measurement volume 509. A microscope objective 509 of the image probe receiver is inserted into the flow through window 505 close to the centerline of the pipe 501 to receive the light from the measurement volume 509 while minimizing flow blockage, to avoid cavitation, and flow stagnation. For one embodiment, one or more tubes having windows at the ends are inserted into the flow to have the measurements made close to the centerline without interference by other contaminants in the optical path.

As shown in FIG. 5, the LED and microscope objective windows face each other in the imaging system with minimized blockage in the main flow. A laser beam is oriented at about 70° off-axis for phase detection using glare spots which are very intense for bubbles comparing to other contaminants, as described in further detail below.

Referring back to FIG. 4, pipe 401 includes a window 416 for a receiver of the IR light absorption system. As shown in FIG. 4, window 416 is at the opposite side of the pipe 401 relative to the window 405. As shown in FIG. 4, a main board 419 and an interface board 421 are coupled to the pipe 401. For one embodiment, main board 419 and interface board 421 have similar mechanical characteristics but different electronic functionalities. For one embodiment, main board 419 and interface board 421 are mounted on top of each other on the base plate, such as base plate 304.

Figure 6:
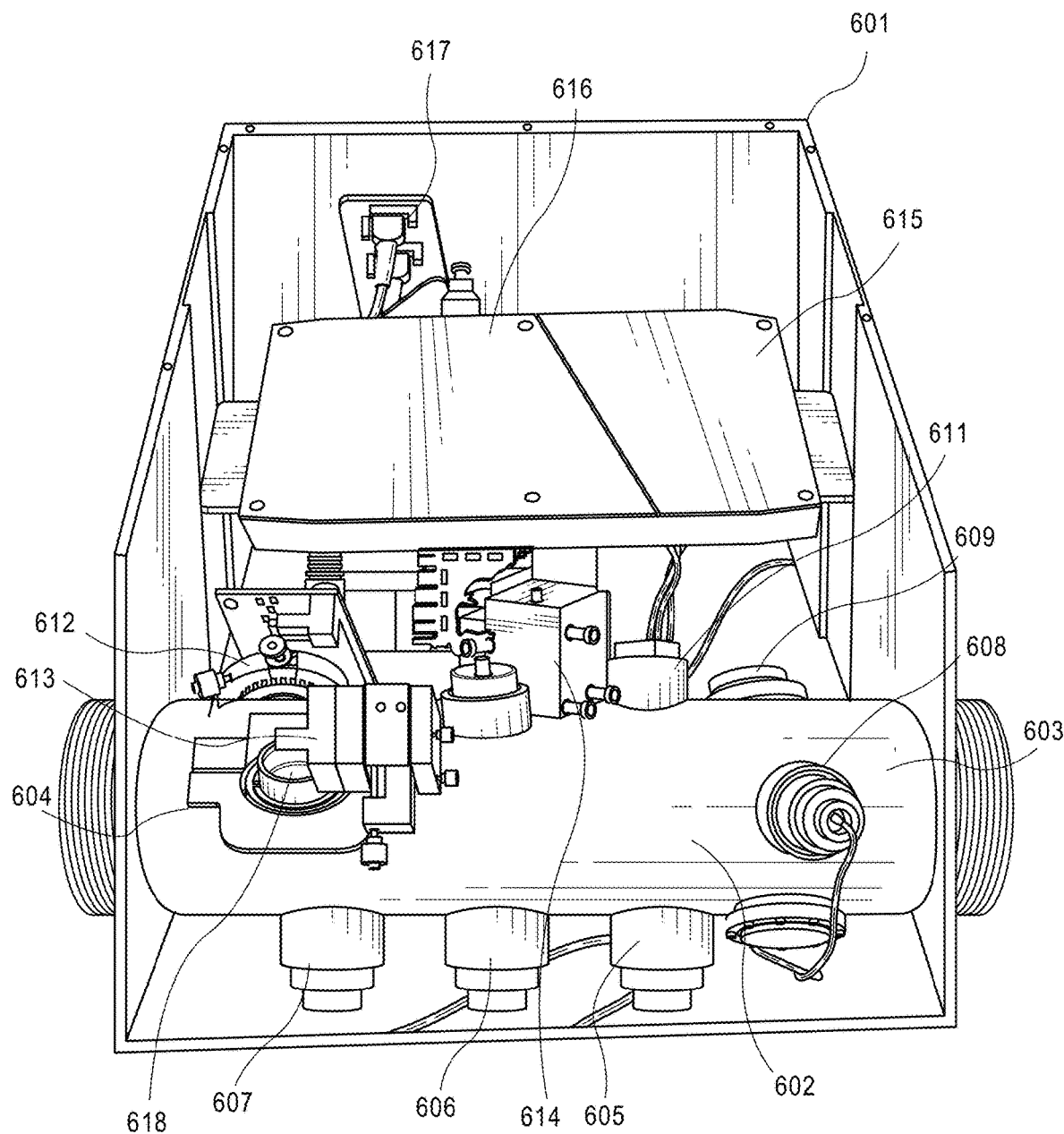
FIG. 6 is a view illustrating of a system to detect contaminants in the fuel flow.

FIG. 6 is a view 600 illustrating of a system to detect contaminants in the fuel flow. The system comprises an enclosure 601 that includes a flow pipe 602 and a compact data processing system 616 on a fixture 615. Data processing system 616 is a digital signal processor, or other processing system. As shown in FIG. 6, flow pipe 602 extends through the enclosure 601 and has threaded ends to attach to a fuel flow line. The pipe 602 includes an input 604 to receive a fuel flow and an output 603 to output the fuel flow. Pipe 602 includes a plurality of windows e.g., windows 605, 606, 607, 608, 609, 611 and 618. For one embodiment, pipe 602 represents pipe 401. The system includes movable stages—e.g., a movable stage 612, a movable stage 613 and a movable stage 614. For one embodiment, the movable stages are used to move optical elements including light sources, receivers, and other optical elements of the system along at least two axes, as described above. For one embodiment, the movable stages are used to rotate optical elements including light sources, receivers, and other optical elements of the system around at least one axes, as described above. For one embodiment, window 618 represents the image probe window 417. As shown in FIG. 6, a connector board 617 is attached to enclosure 601 to electrically connect receivers and light sources of the system to other electronic devices.

As shown in FIG. 6, the imaging system that is in line with the main flow beneficially provides a compact packaging. For one embodiment, the overall size of the enclosure 601 is about 356 mm×261 mm×210 mm that makes the instrument more portable, rugged, and flexible for different configurations comparing to conventional systems. For one embodiment, the thickness of the walls of the enclosure 601 is about 0.25 inches. For one embodiment, enclosure 601 is an aluminum enclosure.

Referring back to FIG. 1, multi-angle light scattering system 106 provides contaminants discrimination via a multi-angle light scattering. For one embodiment, angular distributions of the scattering intensities for bubbles (air or gas) into a fuel, water drops into the fuel, and solid particles (e.g., silica, or other particles) into the fuel are calculated using the Mie scattering theory.

Figure 7A:
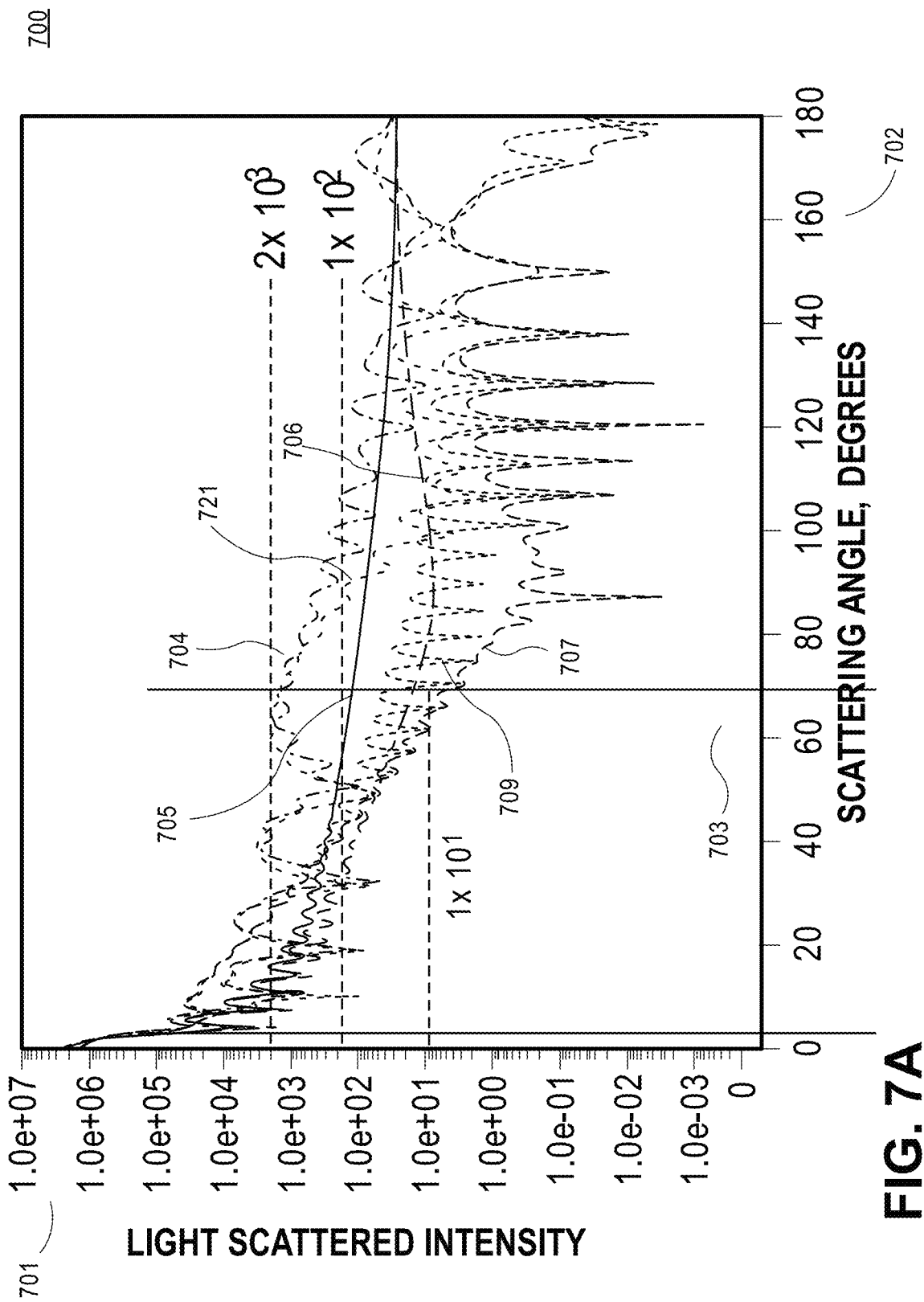
FIG. 7A is an example of a graph showing a light scattering intensity versus a scattering angle for solid particles, water droplets, and bubbles in a fuel at perpendicular and parallel polarizations.

FIG. 7A is a view 700 of an example of a graph showing a light scattering intensity 701 versus a scattering angle 702 for solid particles (705, 706), water droplets (707, 709), and bubbles (704, 721) in a fuel at perpendicular and parallel polarizations. As shown in FIG. 7A, selection of the appropriate light scattering angle of the incident light produces a light scattering difference of approximately an order of magnitude for each of the materials. As shown in FIG. 7A, at a scattering angle of about 70 degrees bubbles produce a light scattering intensity that is about 2 orders of magnitude greater than that produced by free water droplets or solid particles. That is, by selecting appropriate light scattering angles, the separation between the solid particles, free water droplets, and bubbles are each approximately an order of magnitude. At a large light scatter detection angle of approximate 70 degrees, the light scattering is primarily by reflection and refraction so the different solid particles scatter light according to their respective relative index of refraction (material index of refraction to fuel index of refraction). As shown in FIG. 7A, about an order of magnitude separation in the scattering light intensities allows reliable identification of the type of the contaminant producing the light scattering.

Figure 7B:
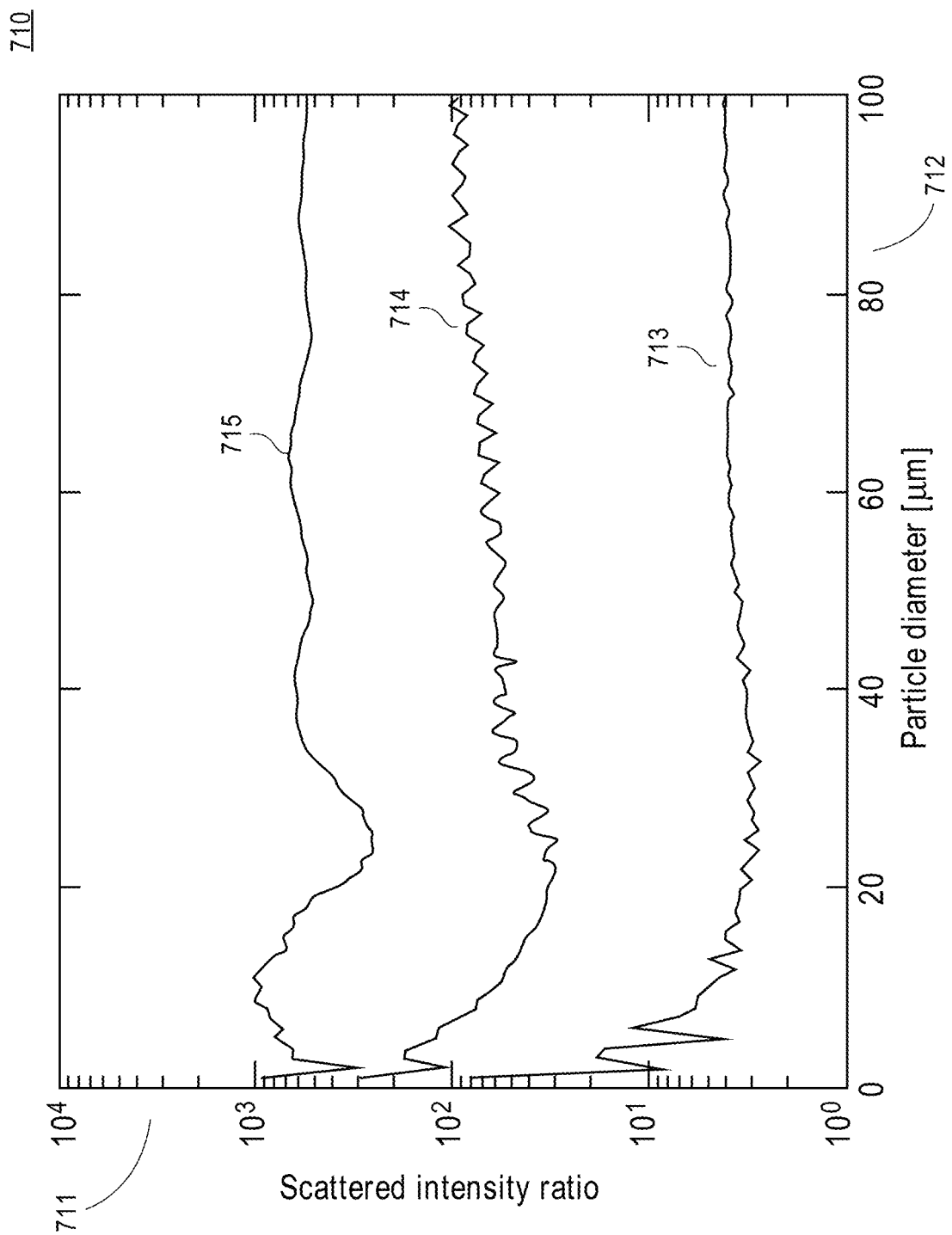
FIG. 7B is an example of a graph showing a light scattering intensity ratio versus particle diameter for bubbles, solid particles, and water droplets in a fuel.

FIG. 7B is a view 710 of an example of a graph showing a light scattering intensity ratio 711 versus particle diameter 712 for bubbles (713), solid particles (714), and water droplets (715) in a fuel. The ratio of the scattering amplitude was collected at 20 degrees and 80 degrees off the forward scattering direction (0 degrees). Collection angle for both collected signals is about 150 mrad. As shown in FIG. 7B, the scattered intensity ratios for bubbles, solid particles and water droplets are different over the entire size range represented. For one embodiment, the multi-angle light scattering intensity technique detects individual contaminants, identifies the material of the individual contaminants, and produces a count of each contaminant passing the measurement volume.

Figure 7C:
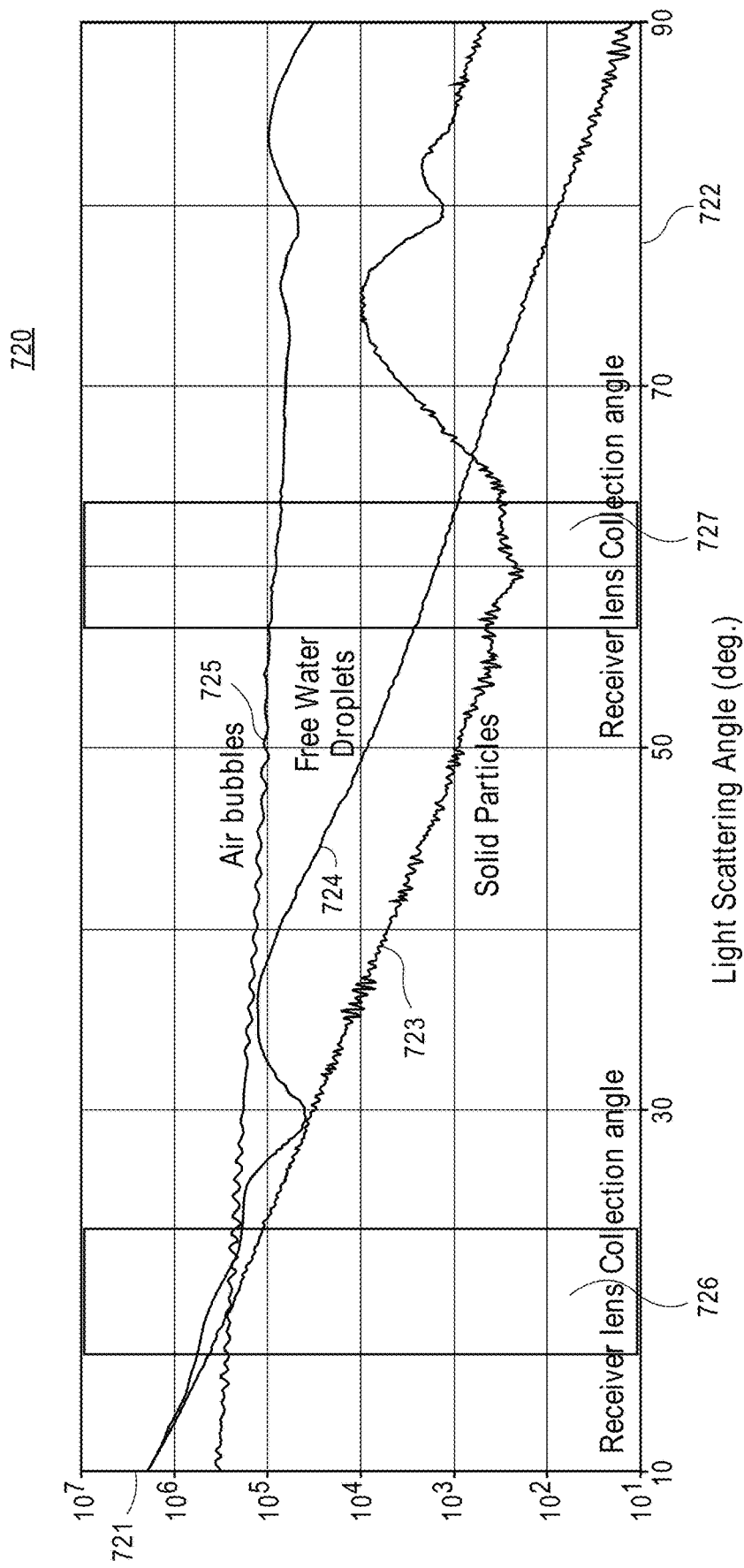
FIG. 7C is an example of a graph showing a light scattering intensity versus a light scattering angle for solid particles, free water droplets, and air bubbles in a fuel.

FIG. 7C is a view 700 of an example of a graph showing a light scattering intensity 721 versus a light scattering angle 722 for solid particles 723, free water droplets 724, and air bubbles 725 in a fuel. FIG. 7C illustrates the light scattering at two collection angles that indicate the receiver lens locations. As shown in FIG. 7C, the light scattered intensities for solid particles 723, free water droplets 724, and air bubbles 725 are approximately equal at small receiver lens collection angles. As shown in FIG. 7C, the light scattering intensities are substantially different for solid particles 723, free water droplets 724, and air bubbles 725 at large receiver lens collection angles. As shown in FIG. 7C, the light scattering intensity of air bubbles 725 is greater than that of free water droplets 724 by about a factor of 100, and the light scattering intensity of free water droplets 724 is greater than that of solid particles 723 by about a factor of 10 at receiver lens collection angles 727 that are in an approximate range from about 57 degrees to about 70 degrees. As shown in FIG. 7C, the light scattering intensity of air bubbles 725 is greater than that of solid particles 723 by about a factor of 10 and the light scattering intensity of solid particles 723 is greater than that of the free water droplets 724 by about a factor of 10 at receiver lens collection angles of about 70 degrees. The use of the multi-angle light scattering detection technique to discriminate bubbles from other contaminants in the fuel allows the system to avoid unnecessary shutdowns of fueling due to the bubbles in the fuel which are harmless.

For another embodiment, the fuel flow is stopped when the multi-angle light scattering detection technique detects gas bubbles in an amount greater than a predetermined threshold, as a large amount of gas in the flow might indicate another issue (pump failure, leak, etc.) that the user might want to look into.

Referring back to FIG. 1, the processor 109 controls the multi-angle light scattering system 106 to provide the multi-angle light scattering detection of contaminants in the fuel flow. The processor 109 is configured to determine a first light scattering intensity from the contaminants in the fuel flow at a first scattering angle. For one embodiment, the first scattering angle is in an approximate range from about 0 degrees to about 180 degrees. For one non-limiting example, the first scattering angle is in an approximate range from about 10 degrees to about 20 degrees off the forward scattering direction (0 degrees). For one embodiment, the light scattering intensity at the first scattering angle is similar to all types of contaminants. The processor 109 is configured to determine a second light scattering intensity from contaminants in the fuel flow at a second scattering angle that is different from the first scattering angle. For one embodiment, the second scattering angle is in an approximate range from about 50 degrees to about 80 degrees. For one embodiment, the second scattering angle is in an approximate range from about 60 degrees to about 80 degrees off the forward scattering direction (0 degrees). For another embodiment, the second scattering angle is in an approximate range from about 120 degrees to about 140 degrees. For one embodiment, the light scattering intensity at the second scattering angle is different for each type of the contaminants. The processor 109 is configured to compare the first light scattering intensity and the second light scattering intensity. For one embodiment, the processor 109 configured to determine a ratio of the second light scattering intensity to the first light scattering intensity.

For one embodiment, the processor 109 is configured to identify one or more bubbles in the fuel flow, if the ratio is substantially equal to a first predetermined ratio. For one embodiment, the first predetermined ratio is in an approximate range from about 1 to about 10. For one embodiment, the processor 109 is configured to identify one or more bubbles in the fuel flow, if the first light scattering intensity and the second light scattering intensity are substantially similar.

For one embodiment, the processor 109 is configured to identify one or more solid particles in the fuel flow if the ratio is substantially equal to a second predetermined ratio. For one embodiment, the second predetermined ratio is in an approximate range from about 30 to about 100. For one embodiment, the processor 109 is configured to identify solid particles in the fuel flow, if the second light scattering intensity is about 10 times greater than the first light scattering intensity.

For one embodiment, the processor 109 is configured to identify one or more water droplets in the fuel flow and passing the detection region, if the ratio is substantially equal to a third predetermined ratio. For one embodiment, the third predetermined ratio is in an approximate range from about 130 to about 1000. For one embodiment, the processor 109 is configured to identify one or more water droplets in the fuel flow passing the detection region if the second light scattering intensity is about 100 times greater than the first light scattering intensity.

Figure 8:
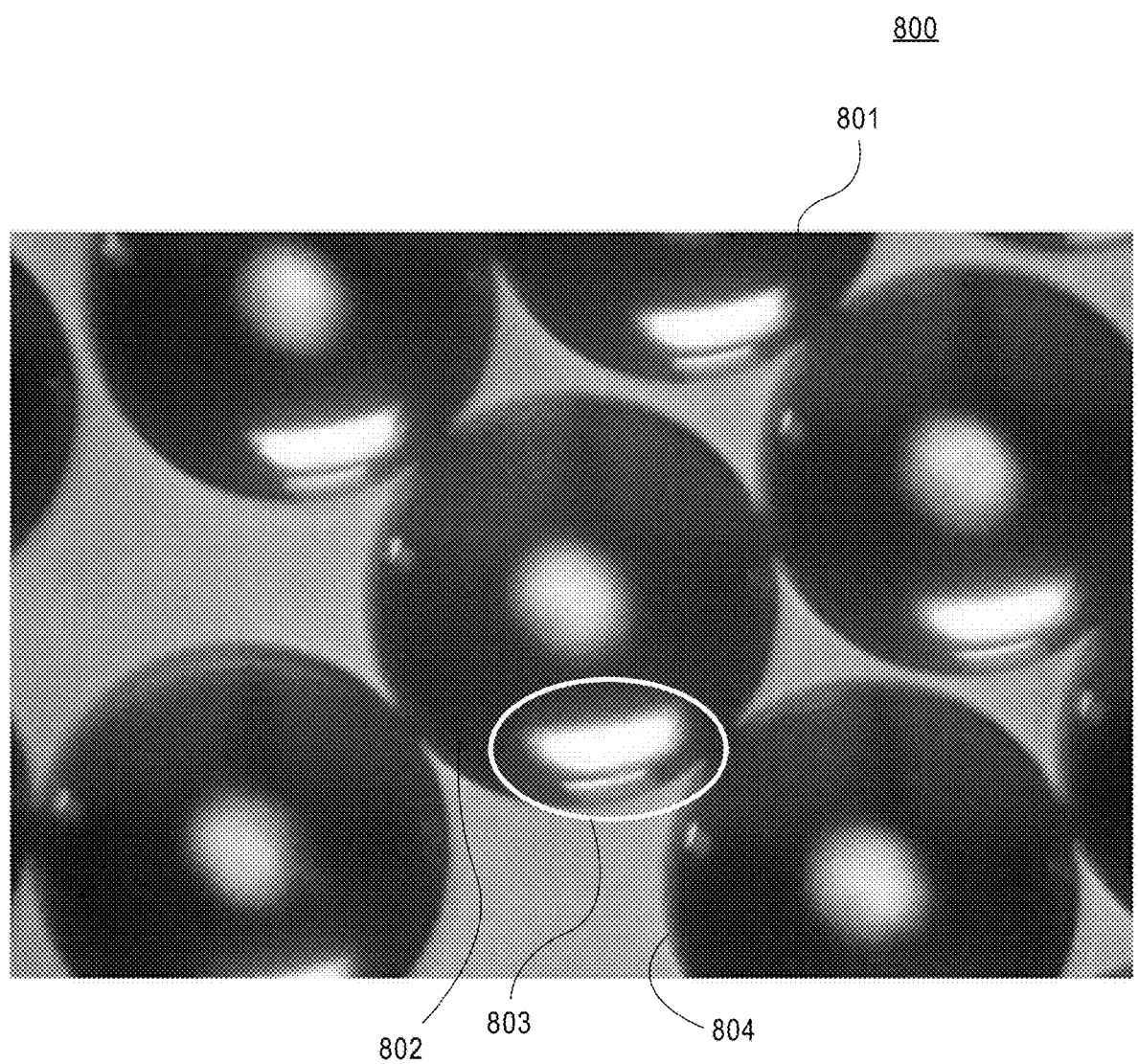
FIG. 8 shows an example of bright field images of contaminants that are illuminated at a large incident angle.

FIG. 8 is a view 800 showing an example of bright field images 801 of contaminants that are illuminated at a large incident angle according to one embodiment. As shown in FIG. 8, a bright field image 803 of bubble has a bright glare spot 803. This glare spot is used to discriminate bubble images from free water droplet images, such as an image 804 in fuel. The imaging system 107 uses the light scattering system 104 to discriminate the images of bubbles from that of the water droplets in a fuel. Water droplets in the fuel have relative index of refraction given as 1.33/1.45 which is equal to 0.917. Air bubbles in the fuel have relative index of refraction of 1.0/1.45 which is equal to 0.69. At a relatively large light scattering angle, air bubbles scatter approximately four orders of the magnitude ($10^4$) more light than water droplets in fuel. For one embodiment, an intense diode laser beam is directed into the fuel flow with a detection angle of the receiver at approximately 70° and coincident with the imaging sample volume. The laser beam produces a very bright glare spot on the bubble images, such as glare spot 803. Free water droplets do not produce bright glare spots, as shown in FIG. 8. Using the bright glare spots by the imaging system 107 provides a significant advantage in terms of rapidly processing the particle images and discriminating bubbles from free water droplets.

Figure 9:
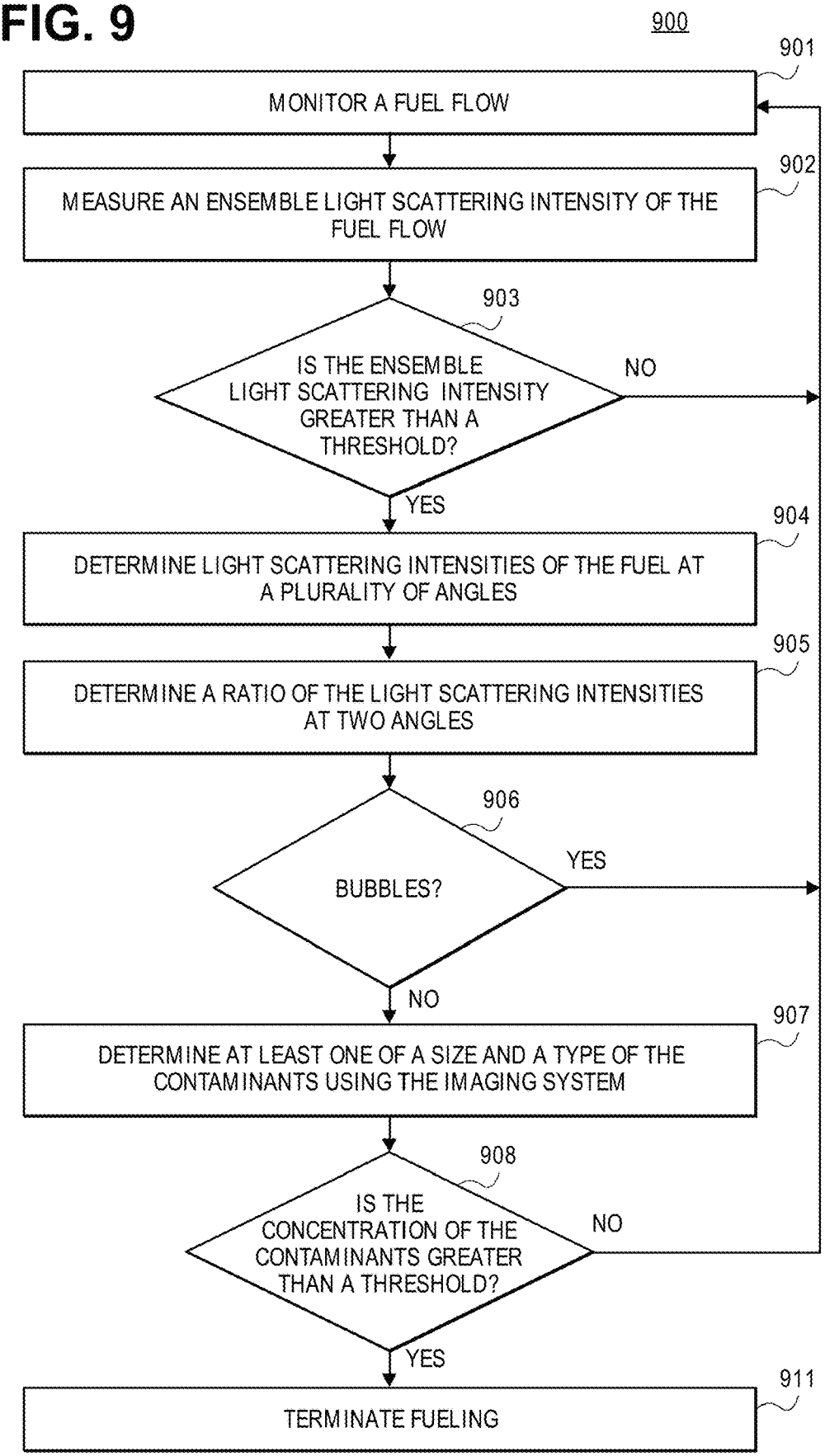
FIG. 9 is a flow chart of one embodiment of a method to detect contaminants in a fuel.

FIG. 9 shows a flow chart of one embodiment of a method 900 to detect contaminants in a fuel. At block 901 a fuel flow is monitored for contaminants using the ensemble light scattering system. At block 902 the ensemble light scattering intensity of the contaminants in the fuel flow is measured. At block 903 it is determined if the ensemble light scattering intensity associated with a large amount of contaminants including gas bubbles, water droplets, and solid particles is greater than a first predetermined threshold. If the measured ensemble light scattering intensity is not greater than the first predetermined threshold, the fueling is continued, and the method 900 returns to block 901. If the measured ensemble light scattering intensity is greater than the first predetermined threshold, at block 903 light scattering intensities from the contaminants in the fuel flow are measured at a plurality of angles using the multi-angle light scattering system, as described above. At block 905 a ratio of the light scattering intensities is determined and the type of contaminants is identified based on the ratio, as described above. At block 906 it is determined if the contaminants are air bubbles, water droplets, or solid particles based on the ratio, as described above. For one embodiment, if the contaminants are air bubbles, the fueling is continued and method returns to block 901. If the contaminants are not air bubbles, at block 907 at least one of a size and a type of the contaminants (e.g., water droplets and solid particles) are determined using the imaging system, as described above. For one embodiment, a size of each of the contaminants is measured and a type of each of the contaminants is identified using the imaging system, as described above. At block 908 the concentration of the contaminants (e.g., water droplets and solid particles) is determined based on at least one of the size and the type of the contaminant. If the concentration of the contaminants is not greater than a predetermined threshold, method 900 returns back to block 901. For one embodiment, if it is determined that the concentration of each of the water droplets and solid particles is less than the predetermined threshold, fueling is continued and method 900 goes back to block 901. For one embodiment, if it is determined that the concentration of the water droplets or solid particles is greater than a predetermined threshold, fueling is terminated at block 911.

Figure 10:
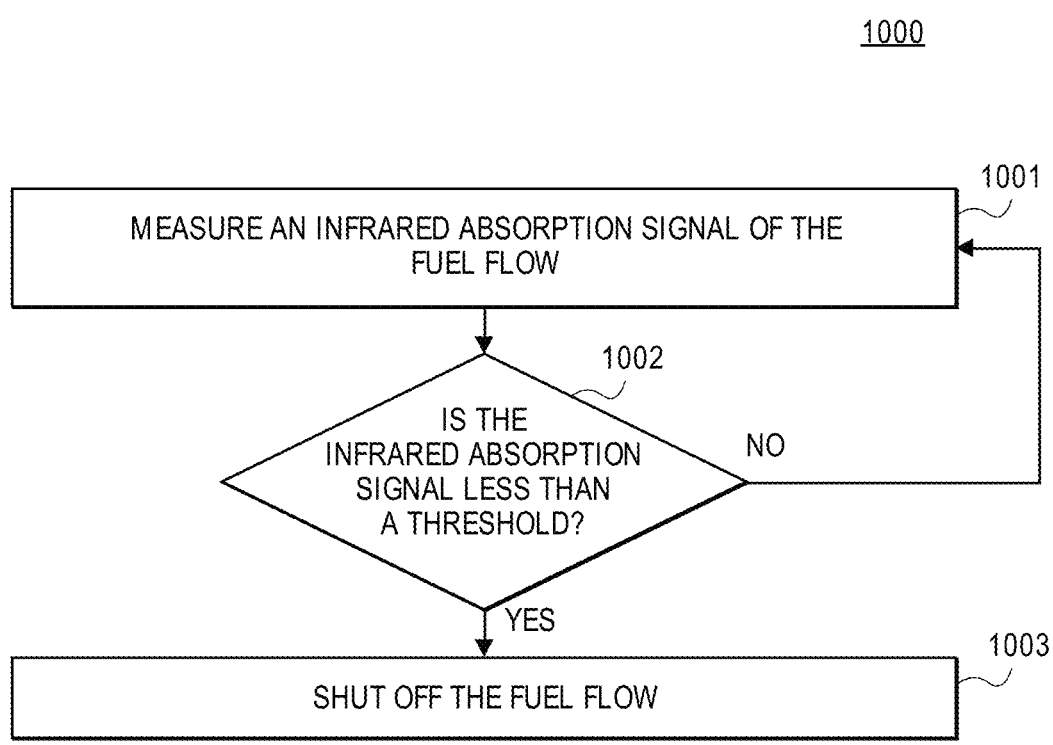
FIG. 10 is a flow chart of one embodiment of a method to detect a large amount of water trapped in a fuel flow.

FIG. 10 shows a flow chart of one embodiment of a method 1000 to detect a large amount of water trapped in a fuel flow. At block 1001 an IR absorption signal associated with the large slugs of water is measured using the IR absorption system. At block 1002 it is determined if the measured IR absorption signal associated with the large amount of water in the fuel flow is less than a predetermined threshold. Generally, the absorption signal extinguishes the transmitted laser beam. In other words, absorption or extinction reduce the laser beam intensity. If the measured IR absorption signal is not less than the predetermined threshold, method 1000 returns to block 1001. If the measured IR absorption signal is less than the predetermined threshold, the fuel flow is shut off at block 1003.

Figure 11:
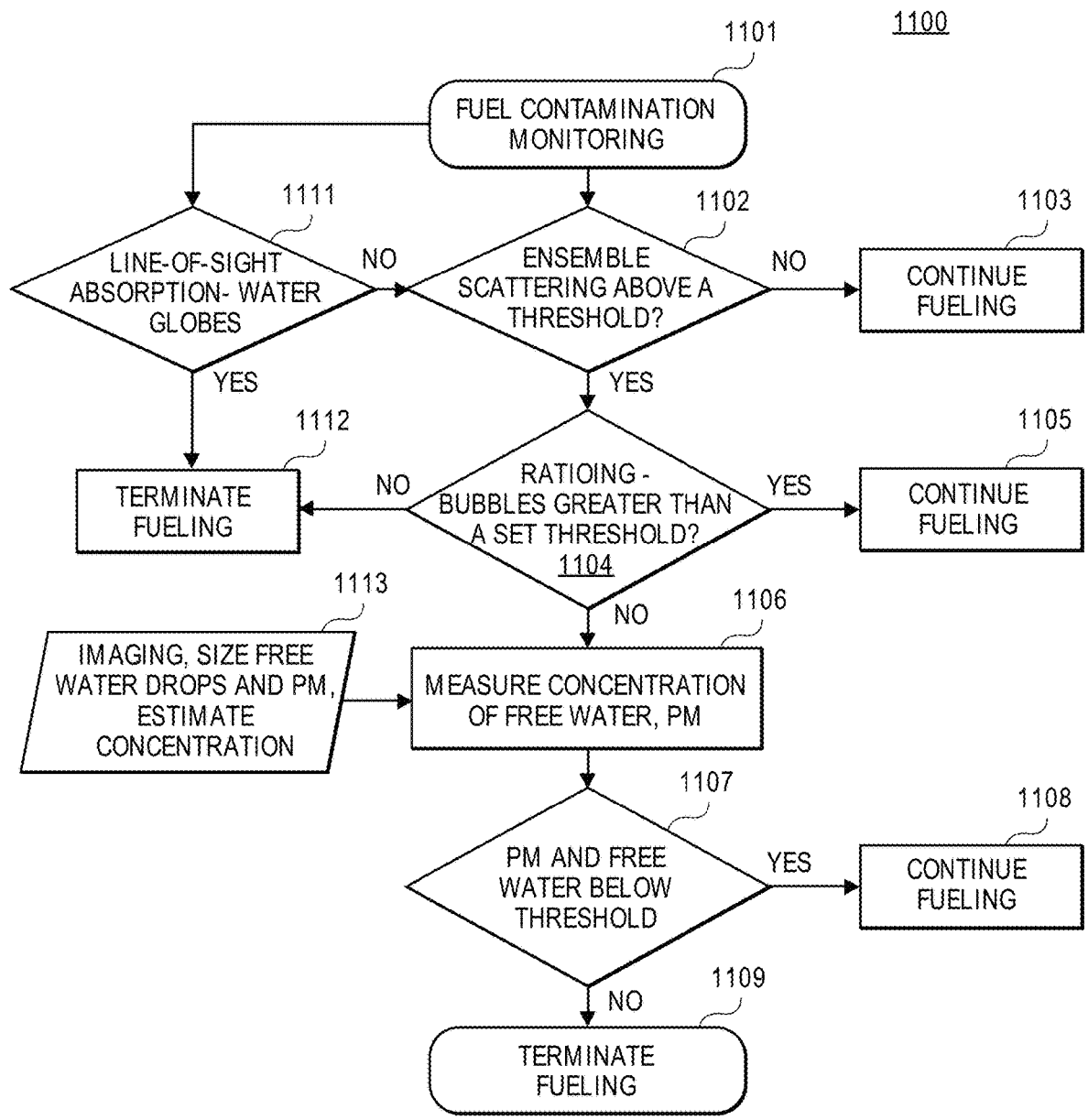
FIG. 11 is a flow chart of one embodiment of a method to detect contaminants in a fuel flow.

FIG. 11 shows a flow chart of one embodiment of a method 1100 to detect contaminants in a fuel flow. At block 1101 fuel contamination is monitored using the IR absorption system and the light scattering system. At block 1102 it is determined by the ensemble laser light scattering if the ensemble scattering is above a first predetermined threshold. If the ensemble scattering is not above the first predetermined threshold, fueling is continued at block 1103. If the ensemble scattering is above the first predetermined threshold it is determined by the light scattering intensity ratio system if a ratio of the light scattering intensities from the contaminants in the fuel flow measured at two different angles is greater than a second predetermined threshold. If the ratio associated with air bubbles in the flow is greater than the second predetermined threshold, the fueling is continued at block 1105. For one embodiment, if the ratio is not greater than the second predetermined threshold, the fueling is terminated at block 1112. For another embodiment, if the ratio is not greater than the second predetermined threshold, the method 1100 goes to block 1106. At block 1106 the concentration of each of the free water droplets and solid particles is measured based on the imaging information provided by the imaging system. The imaging information is determined by the imaging system at block 1113. Determining imaging information includes determining the sizes of the contaminants and identifying types of the contaminants including free droplets and solid particles in the fuel flow, as described above. At block 1107 it is determined if the concentration of the free water droplets and solid particles is below a third threshold. If the concentration of the free water droplets and solid particles is below a third threshold, fueling is continued at block 1108. If the concentration of the free water droplets and solid particles is not below a third threshold, fueling is terminated at block 1109. At block 1111 it is determined using the IR absorption system if the fuel flow has one or more line-of-sight absorption water globes, as described above. If the fuel flow has one or more line-of-sight absorption water globes, the fueling is terminated at block 1112. If the fuel flow does not have one or more line-of-sight absorption water globes, method 1100 goes to block 1102.

Light scattering intensity ratioing used to discriminate the light scattering materials, i.e. free water droplets, solid particles such as sand or metals, and gas bubbles, has been described as based upon single particle detection and analysis. That is, the sample volume is made small enough so that only single particles are detected at one time and their light scattering intensity analyzed. In order for the scattering intensity ratio comparison to be successful, the intensities of the scattered light by the same particle need to be compared by the system at the same time. To ensure that the same particle is simultaneously measured by both the narrow and wide-angle detection systems, the probe volumes need to be carefully selected and set so that the particle is simultaneously observed on both detectors. As an example, a 200 μm focused laser beam diameter is needed to avoid possible particle overlap under acceptable concentration conditions. This imposes a significant challenge in terms of aligning the system and maintaining alignment. In addition, given the relatively large particle size range of the free water droplets, solid particulate matter, and bubbles, the instrument dynamic range is essentially high. For one embodiment, an additional approach is identified that mitigates many of these challenges while providing essential information for identifying harmless bubbles as a source of light scattering.

Ensemble light scattering is used with a single detection angle to obtain a signal that is proportional to the particle concentration (a combination of free water droplets, solid particulate matter, and bubbles, if present). This approach has a significant advantage of compressing the dynamic range requirements for the system by detecting the average light scattered by a large number of particles as opposed to individual particle light scattering. For individual particle light scattering, the scattering intensity is approximately proportional to the particle diameter squared. Thus, if there are individual particles present with sizes ranges of 1 to 100 μm (bubbles may be even larger than 100 μm), the dynamic range of the light scattering intensity will be approximately 1 to 10,000. This range is prohibitive for many detection systems and is also limited by a signal-to-noise ratio. With ensemble scattering, provided there are sufficient numbers of particles to produce a reasonable average, the dynamic range is proportional to the concentration which may only vary over a factor of approximately 10 to 20 times. This is much more manageable in terms of signal detection and processing comparing with conventional techniques. For one embodiment, a ratio of the ensemble light scattering intensities detected at two specified angles is used to identify bubbles in the fuel flow.

For one embodiment, the ensemble light scattering intensity ratio method involves the addition of a second receiver optic and detector at an appropriate angle. For one embodiment, light scattering angles of about 20 degrees and 70 degrees are used for obtaining a very high degree of sensitivity to the light scattering particle material (free water droplets, solid particulate matter, or bubbles). For one embodiment, relatively large apertures are used on the receiver systems to allow observations of light scattered over a length of the laser beam (e.g. from about 1 millimeters (mm) to about 10 mm). A larger collimated laser beam diameter (e.g. from about 1 mm to about 5 mm) is used that leads to much easier alignment and robustness in terms of maintaining adequate alignment of the optics comparing with conventional techniques. For one embodiment, a light beam shaping into a top hat profile using an aperture and relay imaging is used to limit light scattering trajectory effects on the scattered intensities.

Figure 12:
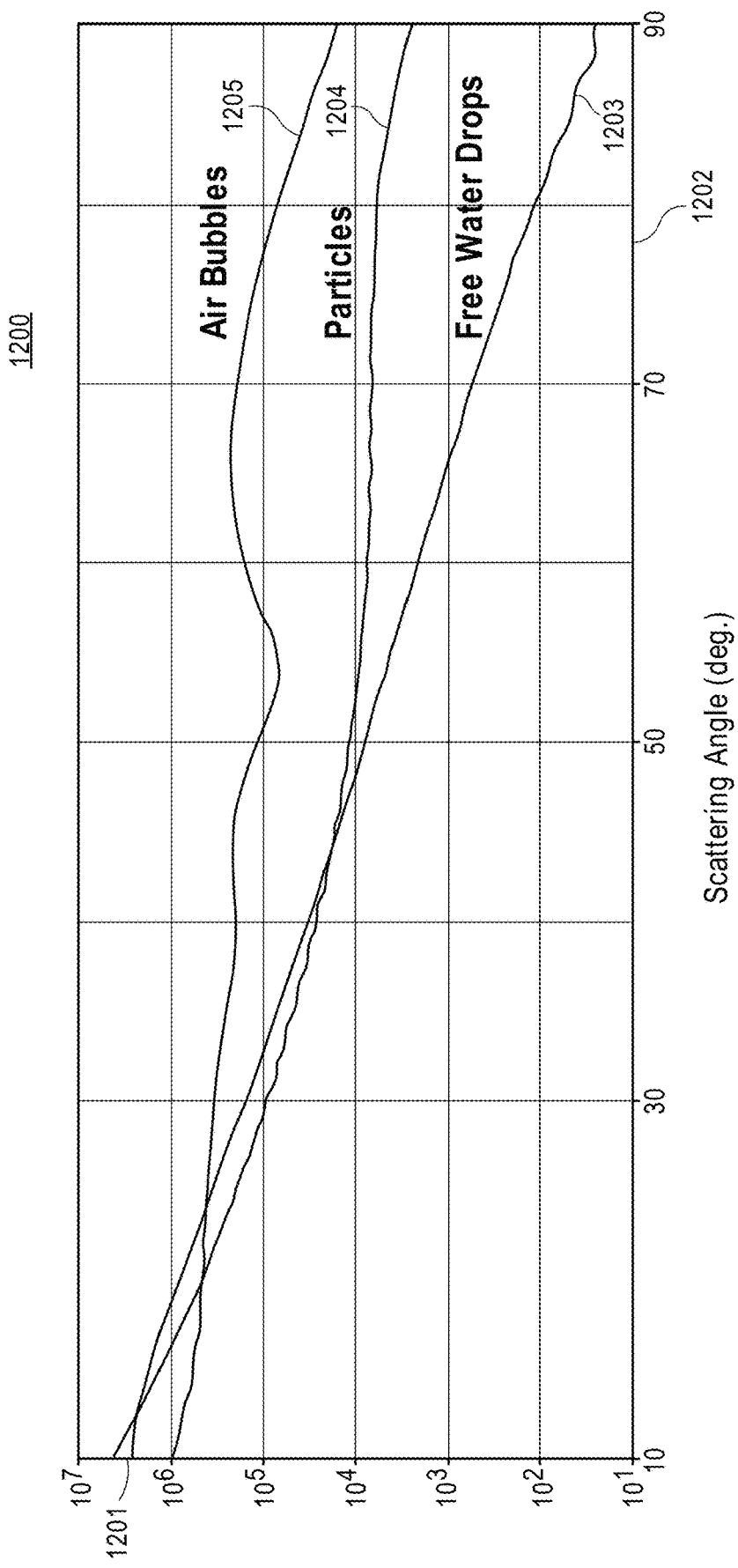
FIG. 12 is a view showing calculated ensemble light scattering intensity versus a light scattering angle according to one embodiment.

FIG. 12 is a view 1200 showing calculated ensemble light scattering intensity 1201 versus a light scattering angle 1202 with mean particle size of 10 microns (μm) and a standard deviation of 20% (e.g., from about 4 μm to about 16 μm diameter) for air bubbles 1205, particles 1204, and free water droplets 1203 according to one embodiment. As shown in FIG. 12, there is a significant separation of approximately an order of magnitude in the light scattering intensity between air bubbles, particles, and free water droplets. With ensemble light scattering, the light scattering intensity is relatively uniform as compared to single particle scattering which shows significant resonances in the scattering intensities. For one embodiment, optimization of the number of parameters including the sample volume size is used to obtain adequate sensitivity and to ensure multiple particles are in the sample volume even under relatively dilute conditions. However, if there are only single bubbles in the measurement volume at any time, the ratio of the light scattering intensity can still be used to identify these light scattering objects as bubbles, particles, or free water droplets.

For one embodiment, when there is only a single light scattering source (particulate material, free water droplets, or bubbles), the ratio method can reliably identify the material present and provide information on the concentration at the same time, if the particle size is also measured using, for example, the imaging approach.

Figure 13:
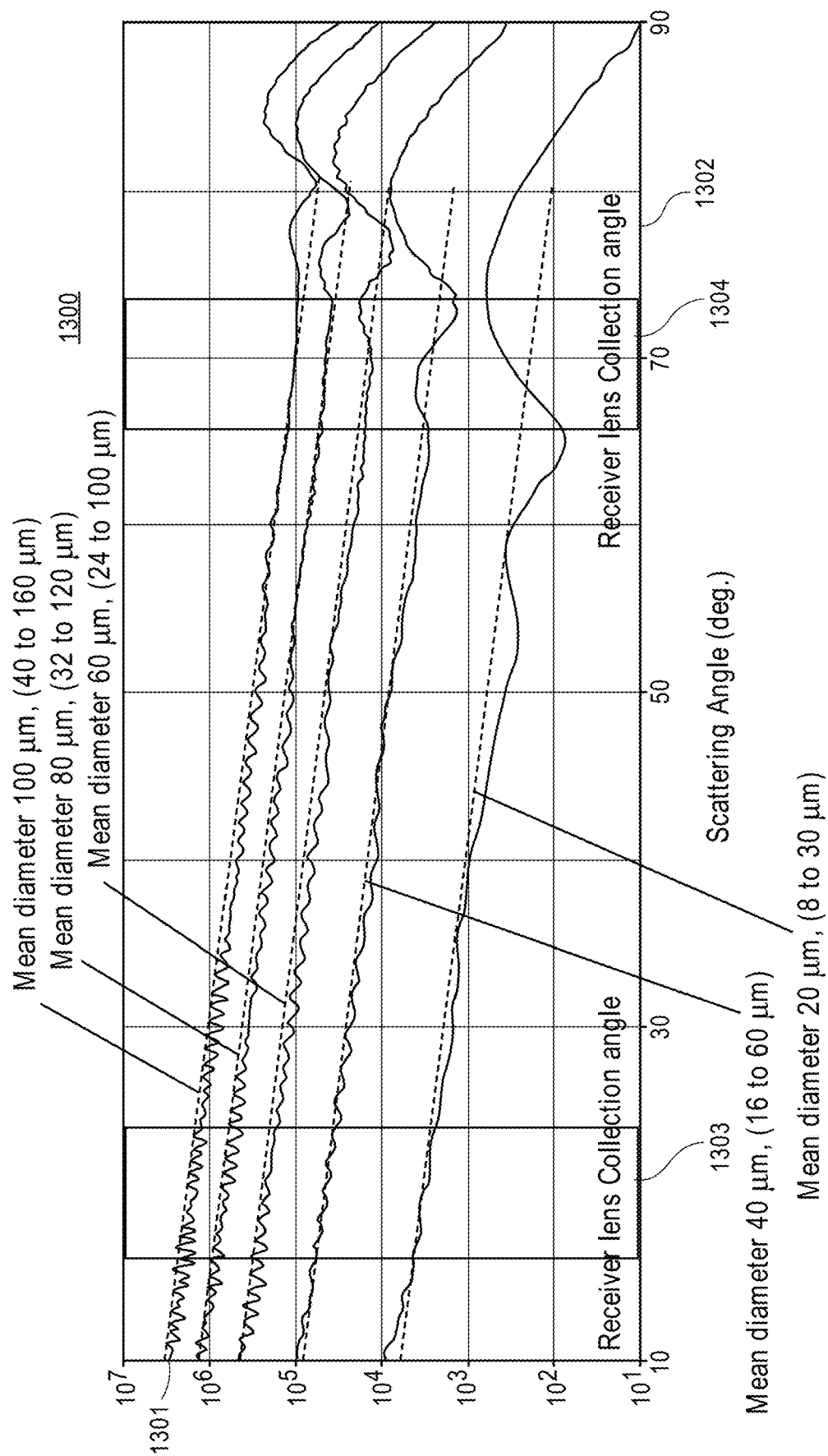
FIG. 13 is a view showing calculated plots of an ensemble light scattering intensity versus a light scattering angle for a range of mean particle sizes according to one embodiment.

FIG. 13 is a view 1300 showing calculated plots of an ensemble light scattering intensity 1301 versus a light scattering angle 1302 for a range of mean particle sizes according to one embodiment. As shown in FIG. 13, the scattered light is computed for ensemble scattering by a plurality of mean droplet sizes (e.g., 20 μm, 40 μm, 60 μm, 80 μm and 100 μm) with a 20% standard deviation. As shown in FIG. 13, the slope of the scattered light intensity 1301 versus scattering angle 1302 is approximately the same for the full range of sizes. FIG. 13 shows locations and angles of collection 1303 and 1304 for two strategically located receiver optics. As shown in FIG. 13, measurements with receiver lenses centered around 20 degrees 1303 and 70 degrees 1304 will produce very similar ratios approximately equal to 4 to 1. As shown in FIG. 13, the light scattering amplitudes (intensities) follow an approximate d^2 increase with a particle diameter d.

Figure 14:
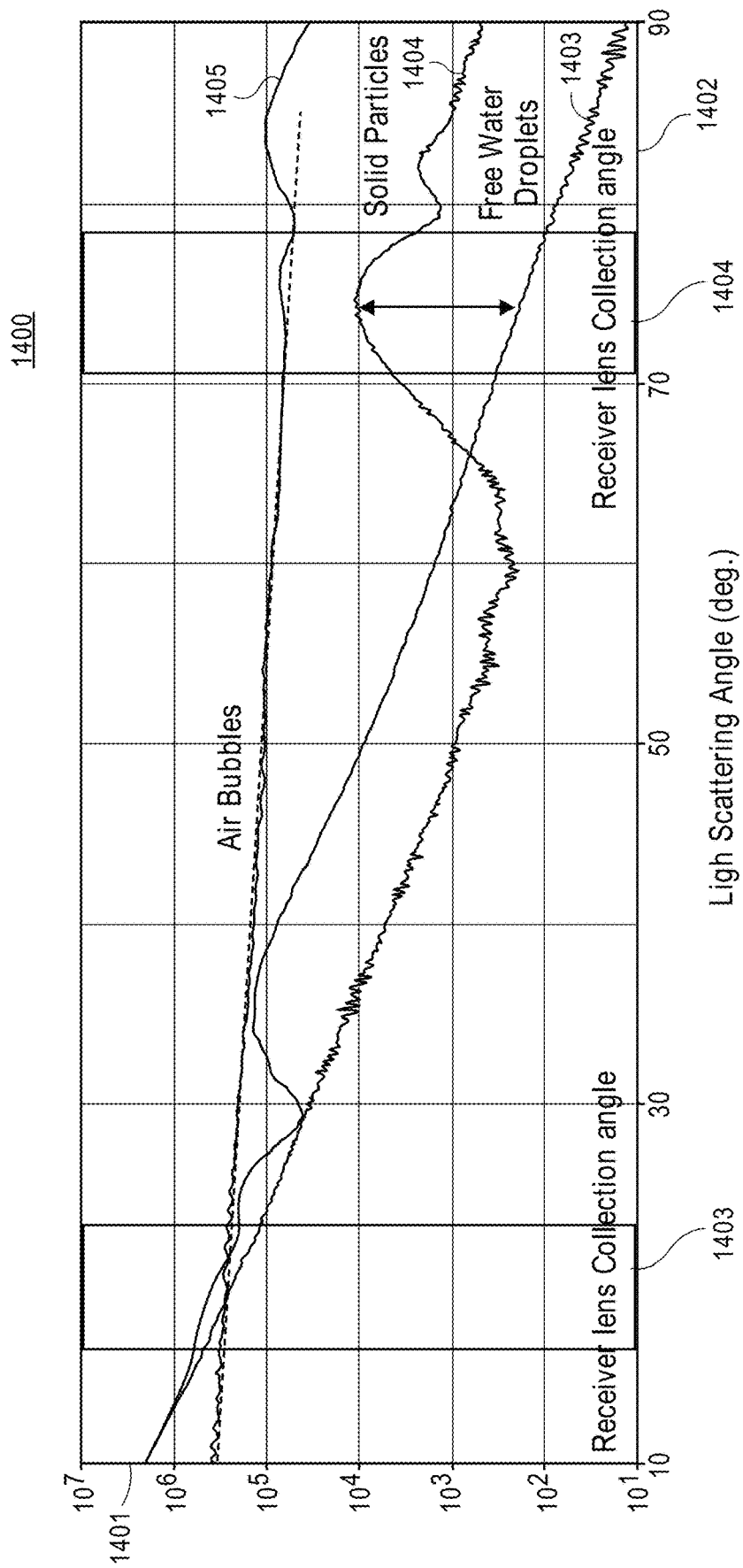
FIG. 14 is a view that shows ensemble light scattering plots for free water droplets, sold particles and air bubbles according to one embodiment.

FIG. 14 is a view 1400 that shows ensemble light scattering plots for free water droplets 1403, sold particles 1404 and air bubbles 1405 according to one embodiment. As shown in FIG. 14, light scattering amplitudes (intensities) at a collection angle of about 75 degrees for free water droplets 1403, sold particles 1404 and air bubbles 1405 are substantially different. As shown in FIG. 14, light scattering amplitudes (intensities) at a collection angle of about 20 degrees for free water droplets 1403, sold particles 1404 and air bubbles 1405 are substantially similar. As shown in FIG. 14, at the collection angle of about 75 degrees the light scattering intensity ratio of air bubbles 1405 is different from that of solid particles 1404 or free water droplets 1403 by at least an order of magnitude. At the collection angle of about 75 degrees the light scattering intensity ratio of solid particles 1404 is different from that of the free water droplets 1403 by approximately an order of magnitude, as shown in FIG. 14. That is, by measuring light scattering intensity at a collection angle of about 75 degrees, faulty termination of fueling can be prevented when only bubbles and perhaps an acceptably low concentration of contaminants exist in the fuel.

For one embodiment, at mixed phase conditions e.g. when at least two of air bubbles, particles and free water droplets are present in the fuel, the light scattering at larger angles produces an increasing intensity ratio with increasing concentrations of solid particles and/or free water droplets relative to the concentration of bubbles. This happen because the light scattered by each material is superimposed to produce the signal. Since the goal of this approach is to primarily detect the presence of a predominance of air bubbles, the deviation from the slope of the ratio for air bubbles can be used as an indication that contaminants are present and hence, the imaging system can be activated to obtain size and concentration measurements. If the imaging system does not show any bubbles present, the intensity ratio can be used as an additional discrimination tool to separate the relative concentrations of solid particulate matter and free water droplets. This possibility is important when the particles and free water droplets are relatively small (less than 10 μm) since such small particles may be difficult to discriminate based on shape. For one embodiment, for a combination of solid particles and free water droplets, the light scattering intensity ratio will vary proportionately, as shown in FIG. 14.

For one embodiment, the ensemble light scattering shows substantial proportionality to particle concentration, once the size distribution has been measured. For an embodiment, for single phase conditions the ensemble light scattering ratio method is used to identify the material and provide redundant concentration measurements (small angle and large angle detection). For one embodiment, the small angle ensemble light scattering is independent of the light scattering material. For one embodiment, if the measured concentrations for the small angle and large angle scattering are different, this is an additional indication that more than one phase (e.g., at least two of bubbles, solid particulate, and free water droplets) present in the fuel.

Figure 15:
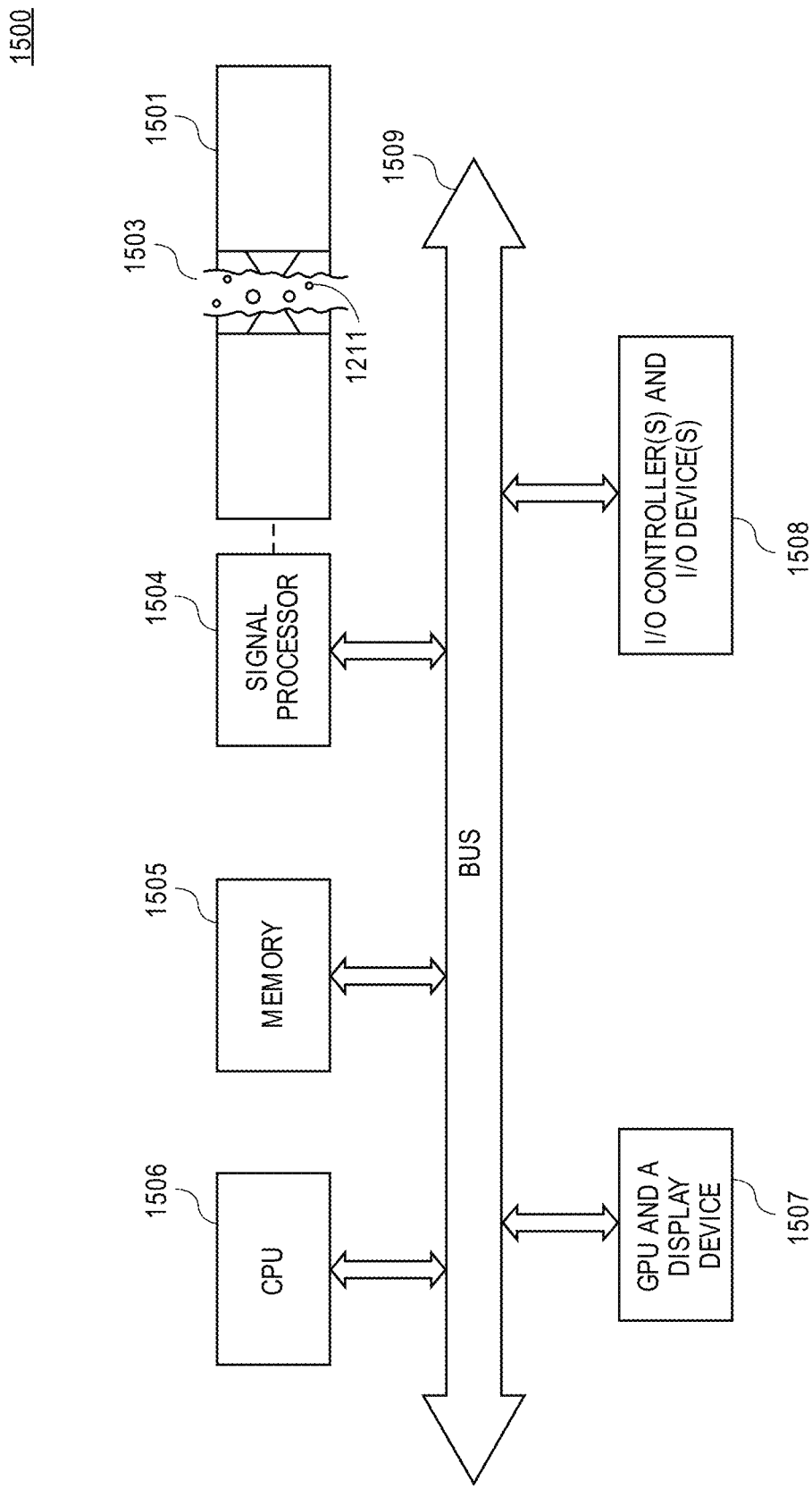
FIG. 15 shows an embodiment of a system to detect contaminants in a fuel.

FIG. 15 is a view showing an embodiment of a system 1500 to detect contaminants in a fuel. System 1500 comprises an apparatus 1501. For one embodiment, apparatus 1501 represents apparatus 100. Apparatus 1501 comprises an input to receive a fuel flow 1503. Apparatus 1501 is configured to detect contaminants 1511 in the fuel flow 1503, as described above. Apparatus 1501 comprises an output to output the fuel flow 1503, as described above. As shown in FIG. 15, apparatus 1501 is coupled to a signal processor 1504. As shown in FIG. 15, a subsystem 1506 comprising a central processing unit ("CPU"), a subsystem 1507 comprising a graphics processing unit ("GPU"), that may be coupled with a display device, one or more subsystems 1508 comprising one or more I/O controllers coupled to one or more I/O devices, a memory 1505 (comprising a volatile RAM, a ROM and a non-volatile memory (e.g., flash memory or a hard drive), or any combination thereof), and a signal processor 1504 comprising a microcontroller are coupled to a bus 1509. At least one of a subsystem 1506 and a signal processor 1504 are configured to perform methods, as described above. Memory 1505 may be used to store data that when accessed by the data processing system, cause the data processing system to perform one or more methods to detect contaminants, as described above.

In the foregoing specification, the invention has been described with reference to specific exemplary embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. An apparatus to detect contaminants in a fuel, comprising:
    an input to receive a fuel flow;
    a light scattering system coupled to the input;
    an imaging system coupled to the light scattering system;
    a memory coupled to the imaging system;
    a processor coupled to the memory; and
    an output to output the fuel flow coupled to the processor, wherein the processor is configured to cause the light scattering system to monitor a light scattering intensity from the contaminants in the fuel flow, wherein the processor is configured to cause the light scattering system to measure the light scattering intensity from the contaminants in the fuel flow; wherein the processor is configured to generate a trigger signal to turn on the imaging system when the light scattering intensity is greater than a predetermined threshold; to determine at least one of a size and a type of the contaminants using the imaging system, and to determine a concentration of the contaminants based on the at least one of the size and the type.

2. The apparatus of claim 1, wherein the processor is further configured to cause the light scattering system to continue to monitor the light scattering intensity from the contaminants in the fuel flow, and wherein the processor is further configured to cause the output to output the fuel flow when the light scattering intensity is not greater than the predetermined threshold.

3. The apparatus of claim 1, wherein the light scattering intensity comprises
    an ensemble scattering intensity from the contaminants.

4. The apparatus of claim 1, wherein the processor is further configured to determine a first light scattering intensity from the contaminants in the fuel flow at a first angle, wherein the processor is further configured to determine a second light scattering intensity from the contaminants in the fuel flow at a second angle, wherein the processor is further configured to determine a ratio of the first light scattering intensity to the second light scattering intensity.

5. The apparatus of claim 1, wherein the contaminants include one or more droplets, one or more solid particles, one or more bubbles, or any combination thereof.

6. The apparatus of claim 1, wherein the light scattering system includes at least two detectors.

7. The apparatus of claim 1, wherein the imaging system includes a pulsed light source.

8. An apparatus to detect contaminants in a fuel, comprising:
    an input to receive a fuel flow;
    a light scattering system coupled to the input;
    an imaging system coupled to the light scattering system;
    a memory coupled to the imaging system;
    a processor coupled to the memory; and
    an output to output the fuel flow coupled to the processor, wherein the processor is configured to cause the light scattering system to monitor a light scattering intensity from the contaminants in the fuel flow, wherein the processor is configured to cause the light scattering system to measure the light scattering intensity from the contaminants in the fuel flow; wherein the processor is configured to generate a trigger signal to turn on the imaging system when the light scattering intensity is greater than a predetermined threshold; to determine at least one of a size and a type of the contaminants using the imaging system, wherein the processor is configured to measure an infrared absorption signal of the fuel flow, and wherein the processor is configured to shut off the fuel flow if the infrared absorption signal is less than a first infrared absorption signal.

9. A method to detect contaminants in a fuel, comprising:
    receiving a fuel flow;
    monitoring a light scattering intensity from the contaminants in the fuel flow using a light scattering system;
    measuring the light scattering intensity using the light scattering system;
    generating a trigger signal to turn on an imaging system when the light scattering intensity is greater than a predetermined threshold;
    determining at least one of a size and a type of the contaminants using the imaging system; and
    determining a concentration of the contaminants based on the at least one of the size and the type.

10. The method of claim 9, further comprising when the light scattering intensity is not greater than the predetermined threshold,
    continuing to monitor the light scattering intensity; and
    outputting the fuel flow.

11. The method of claim 9, wherein the light scattering intensity comprises
    an ensemble scattering intensity from the contaminants.

12. The method of claim 9, further comprising
determining a first light scattering intensity from the contaminants in the fuel flow at a first angle;
determining a second light scattering intensity from the contaminants in the fuel flow at a second angle; and
determining a ratio of the first light scattering intensity to the second light scattering intensity.

13. The method of claim 9, wherein the contaminants include one or more droplets, one or more solid particles, one or more bubbles, or any combination thereof.

14. The method of claim 9, wherein the light scattering system includes at least two detectors.

15. The method of claim 9, wherein the imaging system includes a pulsed light source.

16. A method to detect contaminants in a fuel, comprising:
receiving a fuel flow;
monitoring a light scattering intensity from the contaminants in the fuel flow using a light scattering system;
measuring the light scattering intensity using the light scattering system;
generating a trigger signal to turn on an imaging system when the light scattering intensity is greater than a predetermined threshold;
determining at least one of a size and a type of the contaminants using the imaging system
measuring an infrared absorption signal of the fuel flow; and
shutting off the fuel flow in the infrared absorption signal is less than a first infrared absorption signal.

17. A non-transitory machine-readable medium comprising data that when accessed by a data processing system, cause the data processing system to perform a method to detect contaminants in a fuel, the method comprising:
receiving a fuel flow;
monitoring a light scattering intensity from the contaminants in the fuel flow using a light scattering system;
measuring the light scattering intensity using the light scattering system;
generating a trigger signal to turn on an imaging system when the light scattering intensity is greater than a predetermined threshold;
determining at least one of a size and a type of the contaminants using the imaging system; and
determining a concentration of the contaminants based on the at least one of the size and the type.

18. The non-transitory machine-readable medium of claim 17, further comprising instructions to cause the data processing system to perform operations comprising
when the light scattering intensity is not greater than the predetermined threshold,
continuing to monitor the light scattering intensity from the contaminants in the fuel flow; and
outputting the fuel flow.

19. The non-transitory machine-readable medium of claim 17, wherein the light scattering intensity comprises an ensemble scattering intensity from the contaminants.

20. The non-transitory machine-readable medium of claim 17, further comprising instructions to cause the data processing system to perform operations comprising
determining a first light scattering intensity from the contaminants in the fuel flow at a first angle;
determining a second light scattering intensity from the contaminants in the fuel flow at a second angle;
determining a ratio of the first light scattering intensity to the second light scattering intensity.

21. The non-transitory machine-readable medium of claim 17, wherein the contaminants include one or more droplets, one or more solid particles, one or more bubbles, or any combination thereof.

22. The non-transitory machine-readable medium of claim 17, wherein the light scattering system includes at least two detectors.

23. The non-transitory machine-readable medium of claim 17, wherein the imaging system includes a pulsed light source.

24. A non-transitory machine-readable medium comprising data that when accessed by a data processing system, cause the data processing system to perform a method to detect contaminants in a fuel, the method comprising:
receiving a fuel flow;
monitoring a light scattering intensity from the contaminants in the fuel flow using a light scattering system;
measuring the light scattering intensity using the light scattering system;
generating a trigger signal to turn on an imaging system when the light scattering intensity is greater than a predetermined threshold;
determining at least one of a size and a type of the contaminants using the imaging system;
measuring an infrared absorption signal of the fuel flow; and
shutting off the fuel flow in the infrared absorption signal is less than a first infrared absorption signal.

* * * * *